US011986022B2

(12) United States Patent
Doyle et al.

(10) Patent No.: US 11,986,022 B2
(45) Date of Patent: May 21, 2024

(54) ELECTRONIC VAPORIZER WITH AUTOMATED THERMAL PROFILE CONTROL

(71) Applicant: The Kanvas Company Inc., Newport Beach, CA (US)

(72) Inventors: Joseph Gordon Doyle, Fountain Valley, CA (US); Andy Fathollahi, Newport Beach, CA (US); Alexander Wayne Gordon, Irvine, CA (US); Thomas Doyle, Louisville, OH (US)

(73) Assignee: The Kanvas Company Inc., Newport Beach, CA (US)

( * ) Notice: Subject to any disclaimer, the term of this patent is extended or adjusted under 35 U.S.C. 154(b) by 955 days.

(21) Appl. No.: 16/849,890

(22) Filed: Apr. 15, 2020

(65) Prior Publication Data

US 2020/0329775 A1    Oct. 22, 2020

Related U.S. Application Data

(63) Continuation-in-part of application No. 16/389,851, filed on Apr. 19, 2019, now Pat. No. 10,653,187.

(60) Provisional application No. 62/956,151, filed on Dec. 31, 2019.

(51) Int. Cl.
*A24F 40/57*   (2020.01)
*A24F 40/10*   (2020.01)
*A24F 40/42*   (2020.01)
*A24F 40/60*   (2020.01)
(Continued)

(52) U.S. Cl.
CPC .............. *A24F 40/57* (2020.01); *A24F 40/10* (2020.01); *A24F 40/42* (2020.01); *A24F 40/60* (2020.01); *A61M 11/041* (2013.01); *G06Q 30/0633* (2013.01); *A61M 2205/3368* (2013.01); *A61M 2205/3561* (2013.01); *A61M 2205/52* (2013.01)

(58) Field of Classification Search
None
See application file for complete search history.

(56) References Cited

U.S. PATENT DOCUMENTS

| 9,713,345 | B2 | 7/2017 | Farine |
| 10,653,187 | B1* | 5/2020 | Doyle ..................... A24F 40/57 |
| 2003/0056791 | A1 | 3/2003 | Nichols |

(Continued)

*Primary Examiner* — James Harvey
(74) *Attorney, Agent, or Firm* — Orbit IP, LLP

(57) ABSTRACT

Vaporization devices, systems, and methods with automated thermal profile control are disclosed. Thermal profile information for a particular vaporizable material is encoded to control the operation of the vaporizer. The thermal profile is defined by a plurality of set points specified by power/temperature setting for a specified time. The thermal profile may be configured to be applied during a single or multiple inhalations. A thermal profile recipe code containing thermal profile information associated with the vaporizer cartridge and/or vaporizable material contained therein may be used to control the thermal profile. The thermal profile information may be automatically read by or communicated to the vaporizer and used thereby to automatically control the vaporizer heating element to implement the desired thermal profile associated with the vaporization material. User controls/inputs and sensors are provided to facilitate adjustment or adaptation of a thermal profile, including to particular use conditions.

20 Claims, 16 Drawing Sheets

(51) Int. Cl.
*A61M 11/04* (2006.01)
*G06Q 30/0601* (2023.01)

(56) References Cited

U.S. PATENT DOCUMENTS

| | | | |
|---|---|---|---|
| 2005/0045179 A1 | 3/2005 | Faison, Jr. | |
| 2005/0235991 A1 | 10/2005 | Nichols | |
| 2016/0007651 A1 | 1/2016 | Ampolini | |
| 2016/0200463 A1 | 7/2016 | Hodges | |
| 2016/0227838 A1 | 8/2016 | Johnson | |
| 2016/0309788 A1 | 10/2016 | Hawes | |
| 2018/0104214 A1 | 4/2018 | Raichman | |
| 2018/0184722 A1* | 7/2018 | Murison | F04B 43/14 |
| 2018/0279995 A1* | 10/2018 | Doyle | A61B 8/4427 |
| 2019/0053540 A1 | 2/2019 | Baker | |
| 2019/0158938 A1* | 5/2019 | Bowen | H04M 1/72415 |
| 2019/0200675 A1 | 7/2019 | Bache | |
| 2020/0329775 A1* | 10/2020 | Doyle | G06Q 30/0633 |
| 2020/0352249 A1* | 11/2020 | Achtien | A61M 15/0066 |

\* cited by examiner

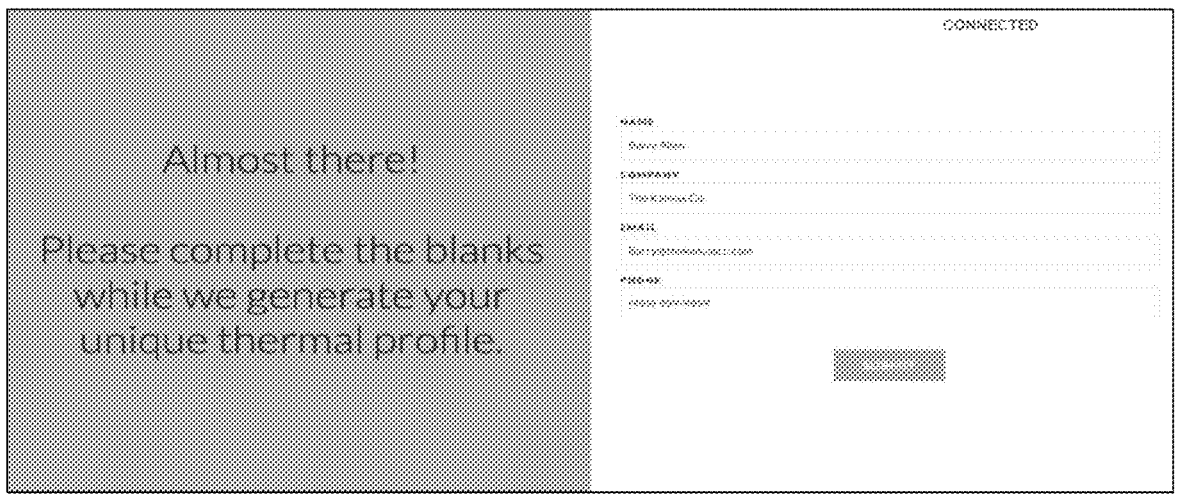
FIG. 8I
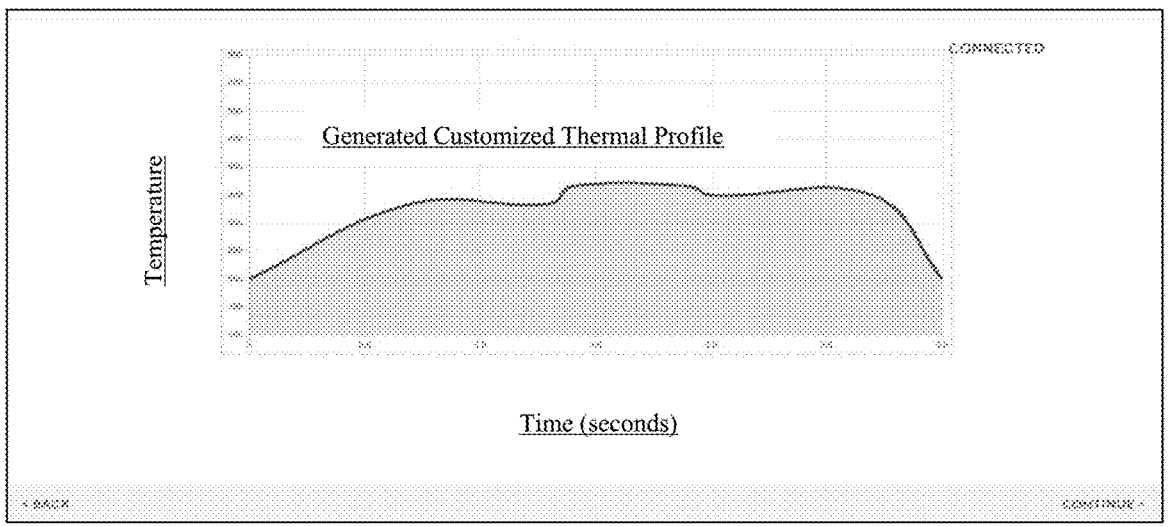
FIG. 8J
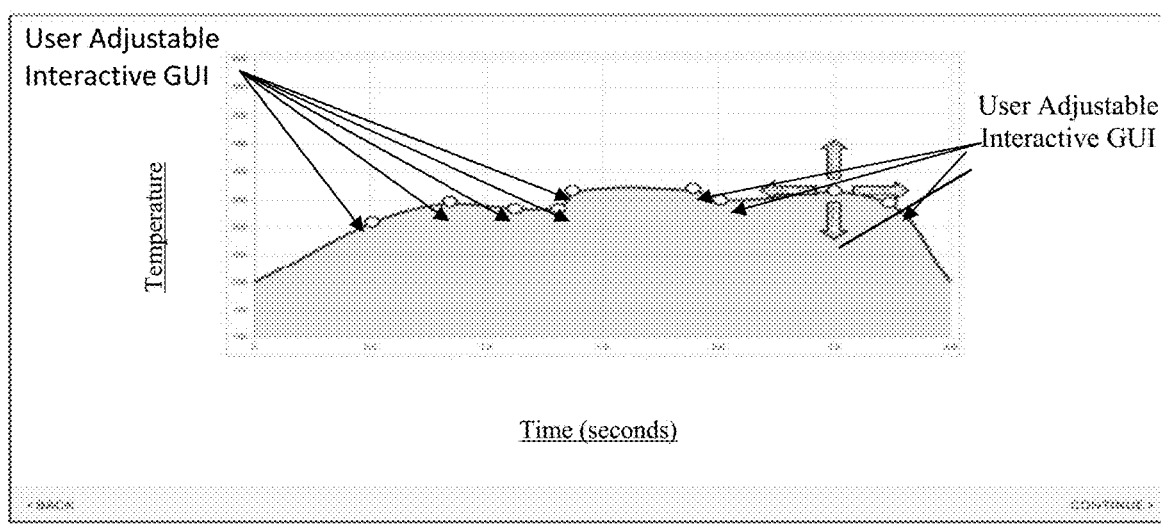
FIG. 8J1

FIG. 10 - Thermal Profile Correlation Table

| Start | 0 | 0.0 |
|---|---|---|
| T1 | 311 | 0.7 |
| T1 | 311 | 0.9 |
| Plume | 410 | 1.0 |
| Plume | 410 | 1.7 |
| End | 200 | 2.0 |

| Start | 0 | 0.0 |
|---|---|---|
| Plume | 410 | 0.7 |
| Plume | 410 | 1.0 |
| T1 | 311 | 1.1 |
| T1 | 311 | 1.7 |
| Plume | 410 | 1.8 |
| Plume | 410 | 2.7 |
| End | 200 | 3.0 |

| Start | 0 | 0.0 |
|---|---|---|
| Plume | 410 | 0.7 |
| Plume | 410 | 1.0 |
| T3 | 350 | 1.1 |
| T3 | 350 | 1.4 |
| T2 | 375 | 1.5 |
| T2 | 375 | 1.9 |
| T1 | 311 | 2.0 |
| T1 | 311 | 2.9 |
| Plume | 410 | 3.0 |
| Plume | 410 | 3.7 |
| End | 200 | 4.0 |

| Start | 0 | 0.0 |
|---|---|---|
| Plume | 410 | 0.7 |
| Plume | 410 | 1.0 |
| T3 | 350 | 1.1 |
| T3 | 350 | 1.8 |
| T1 | 311 | 1.9 |
| T1 | 311 | 3.0 |
| Plume | 410 | 3.1 |
| Plume | 410 | 4.1 |
| T2 | 375 | 4.2 |
| T2 | 375 | 4.7 |
| End | 200 | 5.0 |

| Start | 0 | 0.0 |
|---|---|---|
| Plume | 410 | 0.7 |
| Plume | 410 | 1.3 |
| T2 | 375 | 1.4 |
| T2 | 375 | 2.2 |
| T3 | 350 | 2.4 |
| T3 | 350 | 3.0 |
| Plume | 410 | 3.1 |
| Plume | 410 | 4.0 |
| T1 | 311 | 4.2 |
| T1 | 311 | 4.9 |
| Plume | 410 | 5.0 |
| Plume | 410 | 5.7 |
| End | 200 | 6.0 |

| Start | 0 | 0.0 |
|---|---|---|
| Plume | 410 | 0.8 |
| Plume | 410 | 1.5 |
| T3 | 350 | 1.6 |
| T3 | 350 | 2.4 |
| T2 | 375 | 2.5 |
| T2 | 375 | 3.5 |
| Plume | 410 | 3.6 |
| Plume | 410 | 4.5 |
| T1 | 311 | 4.6 |
| T1 | 311 | 5.9 |
| Plume | 410 | 6.0 |
| Plume | 410 | 6.7 |
| End | 200 | 7.0 |

| Start | 0 | 0.0 |
|---|---|---|
| Plume | 410 | 0.9 |
| Plume | 410 | 1.7 |
| T1 | 311 | 1.9 |
| T1 | 311 | 2.9 |
| T3 | 350 | 3.3 |
| T3 | 350 | 3.9 |
| Plume | 410 | 4.2 |
| Plume | 410 | 4.8 |
| T2 | 375 | 5.0 |
| T2 | 375 | 5.7 |
| T1 | 311 | 6.0 |
| T1 | 311 | 6.4 |
| Plume | 410 | 6.8 |
| Plume | 410 | 7.3 |
| End | 0 | 8.0 |

| Start | 0 | 0.0 |
|---|---|---|
| Plume | 410 | 1.0 |
| Plume | 410 | 1.9 |
| T3 | 350 | 2.1 |
| T3 | 350 | 3.1 |
| T1 | 311 | 3.3 |
| T1 | 311 | 4.0 |
| Plume | 410 | 4.1 |
| Plume | 410 | 5.3 |
| T2 | 375 | 5.4 |
| T2 | 375 | 6.6 |
| T1 | 311 | 6.8 |
| T1 | 311 | 7.7 |
| Plume | 410 | 7.8 |
| Plume | 410 | 8.5 |
| End | 200 | 9.0 |

| Start | 0 | 0.0 |
|---|---|---|
| Plume | 410 | 1.1 |
| Plume | 410 | 2.0 |
| T3 | 350 | 2.1 |
| T3 | 350 | 3.1 |
| T1 | 311 | 3.3 |
| T1 | 311 | 4.0 |
| Plume | 410 | 4.1 |
| Plume | 410 | 5.4 |
| T2 | 375 | 5.5 |
| T2 | 375 | 6.9 |
| T1 | 311 | 7.1 |
| T1 | 311 | 8.1 |
| Plume | 410 | 8.2 |
| Plume | 410 | 9.5 |
| End | 200 | 10.0 |

ELECTRONIC VAPORIZER WITH AUTOMATED THERMAL PROFILE CONTROL

INCORPORATION BY REFERENCE TO RELATED APPLICATIONS

The present application claims benefit of and priority to U.S. Provisional Patent Application No. 62/956,151, filed Dec. 31, 2019. The present application is a continuation-in-part of U.S. patent application Ser. No. 16/389,851, filed Apr. 19, 2019. The above applications are hereby incorporated herein by reference in their entirety.

TECHNICAL FIELD

The field of the invention relates to vaporizing devices, such as electronic vaporizers, and to systems and methods of using, controlling and making such devices that automate or otherwise implement thermal profile control.

BACKGROUND

Vaporizers, also known as electronic vaporizers ("e-vaporizers"), vapes, electronic nicotine delivery systems ("ENDS"), and plant-based vaporization devices, are commonly utilized to vaporize vaporizable material for inhalation by a patient, consumer or other end-user. Such vaporizable material may be comprised of a prescription or over-the-counter ("OTC") pharmaceutical, plant-derived products (e.g., cannabis, herbs, spices, etc.), and a flavoring substance, or combination thereof, which is commonly compounded in a liquid comprised of a propylene glycol, vegetable glycerin, oil, water or some other liquid, or combination thereof.

Conventional vaporizers are typically multi-use devices that are often adapted to vaporize different vaporizable material compositions from a variety of manufacturers/suppliers of those substances. To facilitate vaporization by different vaporizers, manufacturers/suppliers of vaporizable material package their respective vaporizable materials in different containers (e.g., cartridges, pods, etc.) specifically configured and adapted for use with a particular vaporizer device. The end-user of a particular vaporizer adjusts the temperature or power setting of the vaporizer to select the vaporization temperature or power setting that controls the heating element that vaporizes the vaporizable material. The selection process is generally a trial and error iterative process comprised of a user setting an initial power or temperature setting, activating the vaporizer to heat the vaporizable material, inhaling the vaporized material, and repeating until the user finds a temperature or power setting that is acceptable.

The inventors here recognized that this trial and error search for a suitably acceptable temperature is typically performed without sufficient information and understanding of the relevant component elements of the vaporizable materials and/or the operation or performance characteristics of the vaporizer, can be elusive and frustrating to the end-user, results in greatly varying levels of user satisfaction experiences even for the same vaporizable material, and is frequently too simplistic to maximize efficacy or consumer satisfaction as it is insufficient to take into account the differences in vaporization temperatures associated with the individual component elements that comprise a particular vaporizable material and thereby produce less than optimal aerosol compositions that may unnecessarily or unintentionally impact a user's health.

SUMMARY

Consistent with the foregoing, described herein are vaporizer devices, systems and methods that are capable of automating control of the vaporization thermal conditions to provide a consistent consumer experience while taking into account the complexities associated with vaporizing vaporizable materials comprised of a plurality of component elements. The devices, systems and methods disclosed herein, for example, are capable of allowing manufacturers and suppliers of consumable vaporizable materials, who are generally most knowledgeable of the composition and characteristic traits of their respective vaporizable material, to exercise control over how their respective products are consumed consistent with their vested interests in maximizing or otherwise enhancing consumer satisfaction. The vaporized material composition of aromatics (e.g., terpenoids), bio-active and pharmacological components, flavorings, water and/or other components of the vaporizable material contained within the vapor or aerosol inhaled by the user, are thereby capable of being better managed and controlled. Additionally, the vaporizers disclosed herein are capable of eliminating the consumer frustration and waste associated with attempting to set a vaporization temperature and the start-up time and the consumption of vaporized material in a sub-optimal manner associated with doing so.

The subject matter described herein relates to vaporizers that are adapted with the capability of heating a vaporizable material in accordance with a thermal profile associated with a particular vaporizable material, including the constituent components thereof. Particular aspects of the disclosed subject matter relate to the manner by which a thermal profile is (i) determined for a particular vaporizable material, (ii) associated with the vaporizable material, and (iii) communicated and employed in connection with control (including automated control) of the vaporizer. Additional aspects are directed to vaporizer user data, including the capture, storage, communication, analysis and presentation of such data.

A "thermal profile" as used herein refers to a heating profile for a vaporization heating cycle that is associated with generating an aerosol or vapor dose for inhalation (e.g., draw or puff) by a user and is defined by a plurality "set points." A "set point" as used herein is defined by both (i) a specified power and/or temperature setting and (ii) a specified duration of time for that setting and is distinct or different from the temperature/power and time associated with the heating ramp-up or ramp-down profiles of the vaporizer.

Additional details regarding the various aspects of the subject matter described herein are set forth in the accompanying drawings and descriptions below and/or are otherwise apparent therefrom. It should be understood that the descriptions and illustrations herein, while illustrative of the various aspects of the disclosed subject matter, it is the claims that are intended to define the appropriate scope of the protected subject matter.

BRIEF DESCRIPTION OF THE DRAWINGS

The accompanying drawings, which are incorporated in and constitute a part of this specification illustrate certain aspects of the subject matter disclosed herein and together with the description, help explain aspects associated with the disclosed implementations.

FIGS. 2A-2B further illustrate how the external device and/or vaporizer may be in further communication with another external computing device such as a server.

FIG. 10 is an example of a set of thermal profile correlation tables that corresponds to a particular preferences of a user or customer.

DETAILED DESCRIPTION

Figure 1A:
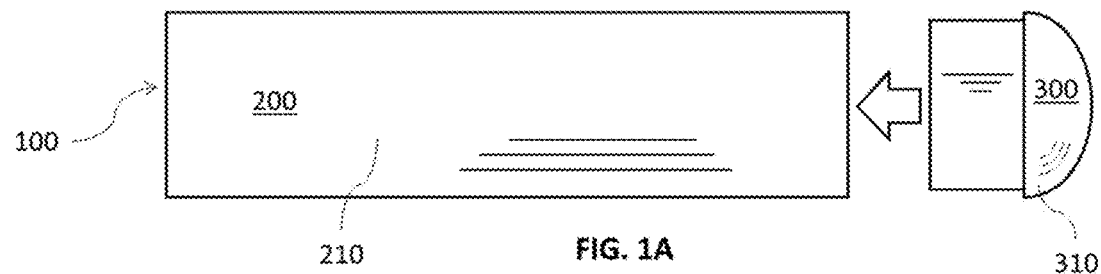
FIGS. 1A-1C illustrates an exemplary two-piece vaporizer generally comprising vaporizer body that controls the heating of a vaporizer cartridge that contains vaporizable material in accordance with the disclosed subject matter.
Figure 1B:
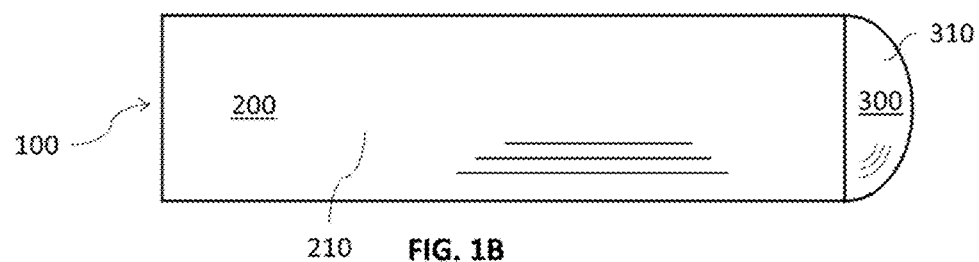

Illustrated in FIGS. 1A-1B is a vaporizer 100 that employs a conventional two-piece configuration comprising a vaporizer body 200 and a reversibly attachable vaporizer cartridge (or pod) 300, each of which being externally defined by a housing or casing 210, 310 respectively that contains and protects electrical, thermal, and other components contained therein. FIG. 1A illustrates the vaporizer 100 with the vaporizer body 200 and vaporizer cartridge 300 being detached from one another. FIG. 1B illustrates the vaporizer 100 with the vaporizer body 200 and vaporizer cartridge 300 attached to one another to facilitate consumer use of the vaporizer 100. The external configuration of the vaporizer cartridge 300 is adapted to being reversibly engaged within a aperture at one end of the vaporizer body 200.

Figure 1C:
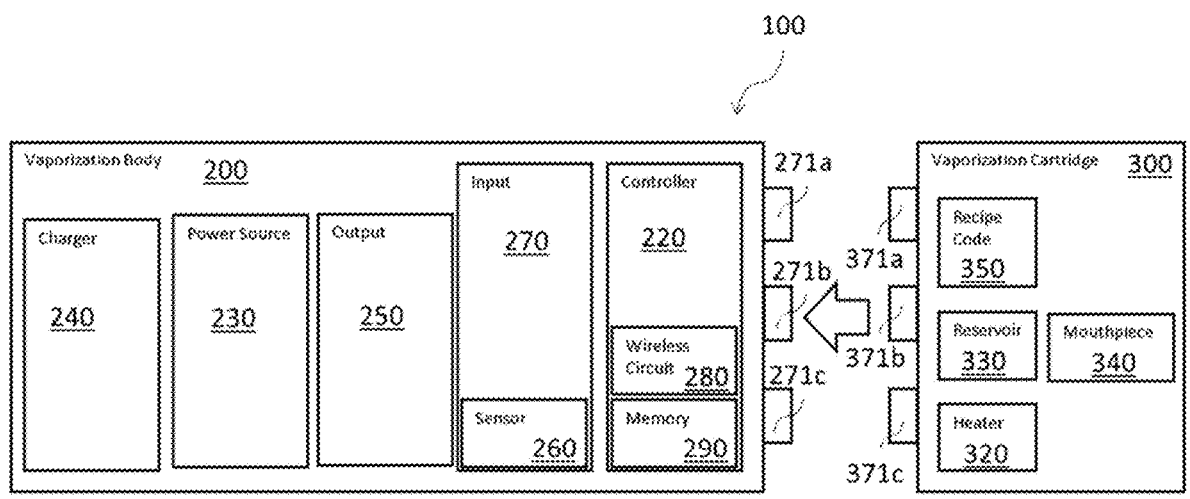

FIG. 1C is a block diagram illustration of the components of the vaporizer 100 with the vaporizer body 200 and vaporizer cartridge 300 detached from one another. The vaporizer body 200 is generally comprised of a controller 220 that controls the application of power or energy from a power source 230 (typically contained within the vaporizer body 200) to the heater 320 contained in the vaporization cartridge 300, which when sufficiently energized heats and vaporizes the vaporizable material that is contained in the reservoir 330 of the vaporizer cartridge 300. The vaporized material (also knowns as "aerosol" or "vapor") is inhaled by the user via an aperture in the cartridge 300 referred to as a mouthpiece 340. The power source 230 may be comprised of any suitable power source including replaceable or rechargeable batteries or power from an external source. A charger (and charging circuit) 240, which may be controlled by the controller 220, may also be provided to power the vaporizer 100 and/or electrically charge a battery. The charger 240 may be a conventional cabled/wired plug-in charger or a wireless charger such as and inductive Qi charger. Vaporizable material is commonly in liquid form but may also be a solid (e.g., wax) or gas or a combination liquid, solid and/or gas.

An externally accessible universal serial bus (USB) connection or other suitable connector may be positioned on the vaporizer housing 210 and electrically connected to the charger and/or controller 205 to facilitate powering the vaporizer 100 (or charging the power source/battery thereof) and/or communication over a wired connection between an external device (e.g., electronic devices 700, 800 illustrated in FIG. 2A) and the controller 220.

The vaporizer 100 may also include one or more inputs 270. Such inputs may be one or more buttons, dials, or other user interfaces and/or one or more controller inputs or sensors 260. The sensors 260 may include accelerometers or other motion sensors, biometric sensors, capacitive sensors, flow sensors, pressure sensors, temperature sensors (e.g., ambient, reservoir, heating element temperature), power sensor, GPS or location trackers, timers or clocks, and other use or control sensors, etc., that detect or receive inputs that are communicated to the controller 220 to control the operation of the vaporizer 100 and/or relate to the use and operation of the vaporizer 100 and the collection of data relating thereto. For example, accelerometers, flow sensors, and clocks may detect and track the duration of a consumer's use (via movement and/or inhalation), whereby the controller 220 consistent with that use activates the vaporizer 100 and facilitates power to the heater 320. Sensors 260 may also detect ambient temperature, reservoir 330 temperature, heater 320 temperature, when and/or whether a cartridge 300 is properly engaged within the vaporizer body 200 (e.g., via magnetic or other physical attachment means), when the vaporizer cartridge 300 is depleted, location data, and/or the orientation of the heater 320 so that power to the heater 320 controlled by the controller 220 can be properly regulated in accordance with the teachings herein and/or use data collected, stored (e.g., in memory 290), communicated (e.g., via a cabled/wired or wirelessly), processed and/or presented. The vaporizer 100 may include a user button or other interface that can reset or erase information stored in memory on the vaporizer 100 and/or effectuate a command or instruction, which when externally communicated, resets or erases use data associated with the vaporizer 100 that is stored in an external device (e.g., 700/800 in FIGS. 2A-2B) associated with the vaporizer 100.

As further illustrated in FIG. 1C, the vaporizer body 200 may further comprise one or more outputs 250, which may comprise one or more optical (e.g., LEDs, displays, etc.), tactile (e.g., vibrational, etc.), or sonic (e.g., piezoelectric, etc.) feedback components, or the like, or some combination thereof that can alert or otherwise communicate certain settings or conditions (e.g., dosage, temperature, power, use, cartridge or vaporizable material identification and information, etc.). Thus, for example, by tracking the use of the vaporizer 100 as described above, an alert or other communication can be provided to the user when the user has reached, is about to reach, or exceeds certain dosages.

As illustrated in FIG. 1C, the vaporizer body 200 and cartridge 300 depicted therein includes one or more opposing complimentary electrical contacts 271a-271c and 371a-371c that engage each other when the vaporizer cartridge 300 is properly engaged for operation with the vaporizer body 200. The electrical contacts 271a-271c and 371a-371c may be of an suitable configuration, such as pins and opposing receptacle, so that when engaged with one another create an electrical circuit between the vaporizer cartridge 300 and body 200. Thus, when the cartridge 300 is properly seated or engaged with the vaporizer body 200, the electrical contacts 271a-271c on the vaporizer body 200 and the electrical contacts 371a-371c on the cartridge 300 form an electrical circuit there-between, the vaporizer 100 is capable of transferring power from the power source 230 to the heater 320 and/or exchange data or communications between the vaporizer body 200 and the cartridge 300 via the electrical circuit.

A wireless circuit 280, which is illustrated in FIG. 1C as being located in the vaporizer body 200, may also be provided to facilitate wireless communication with the vaporizer 100. A memory component 290 is also depicted in FIG. 1C to facilitate the storage of data, including for example control programs (e.g., thermal profile control instructions), use information, and input and sensor information including data, commands and/or instructions.

Figure 2A:
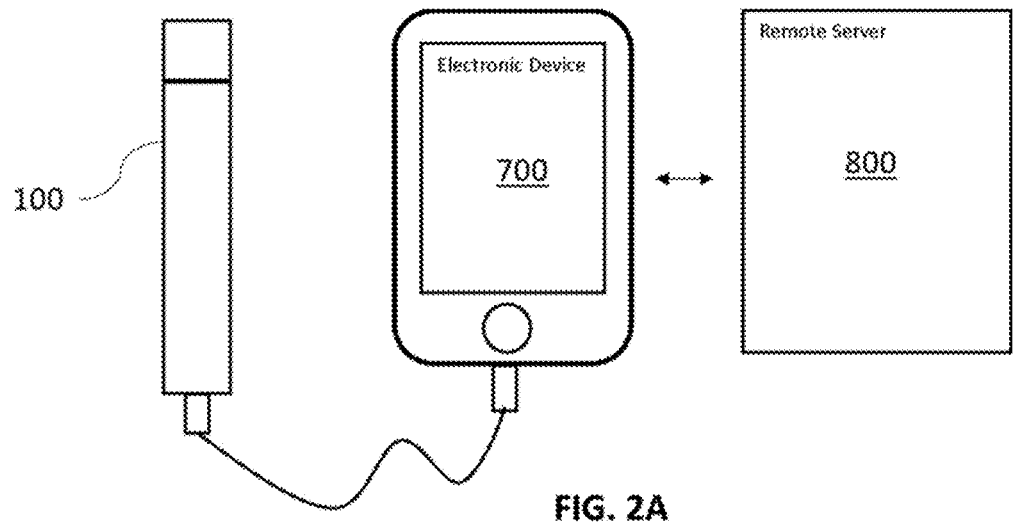
FIGS. 2A-2B illustrate a system where an external device is in communication with the vaporizer via a wired/cabled connection as illustrated in FIG. 2A and via a wireless connection as illustrated in FIG. 2B.
Figure 2B:
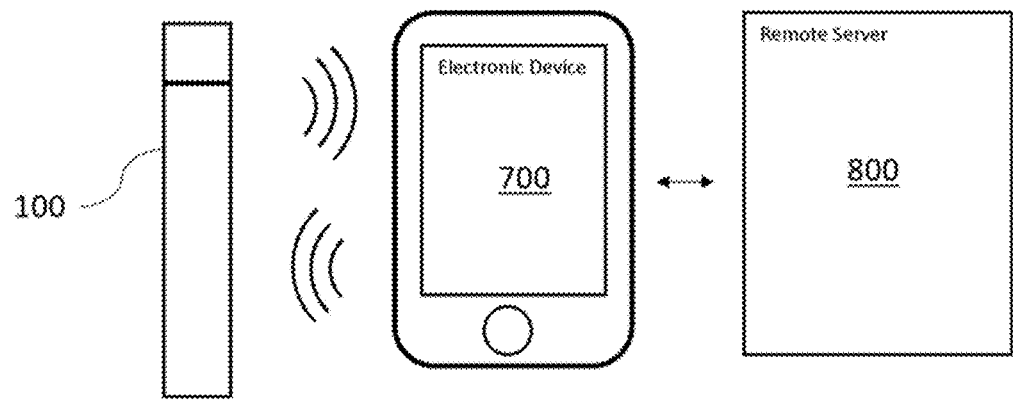

FIGS. 2A-2B illustrate a vaporizer system whereby an external device 700, such as a smart phone or other computing device, may communicate or otherwise exchange data with the vaporizer 100 through a wired/cabled connections (e.g., the USB connector described above) such as that illustrated in FIG. 2A and/or via wireless communication (e.g., Bluetooth or other wireless protocol) with the wireless circuit 280. The external device 700 may in turn communicate and/or otherwise exchange data (via wired and/or wireless communication) with another external computing device such as a server 800. Thus, for example, the external devices 700/800 may be utilized to program the vaporizer 100 (including the vaporizer body and/or vaporizer cartridge) and/or receive data (e.g., use data, such as location, duration, dosage, information on the vaporizable material etc.) from the vaporizer 100.

U.S. Patent Application Publication No. US 2018/0043114 A1 (the Bowen Application), which is hereby incorporated by reference in its entirety, describes in detail vaporizers with similar hardware components to those of the foregoing description of the vaporizer 100 and the operation and structure thereof.

As is recognized herein, the ingredients, ratios, manufacturing methods, and other characteristics of vaporizable material varies greatly. Consequently, how and under what conditions vaporizable material is vaporized can materially impact efficacy of the consumed aerosol and consumer satisfaction. Some conventional vaporizer devices and systems allow users to manually control the power to the vaporizing heating element and thereby set, either directly or indirectly, the vaporization temperature. Some newer vaporizers and vaporizer systems, such as those disclosed in the Bowen Application, include a software application on an external digital device and an "identifier" component by which identification of the cartridge and/or vaporizable material contained within the cartridge may be communicated to the vaporizer to facilitate basic control over the vaporizer.

None of these conventional or newer vaporizers, however, effectuate automated control of the operation of a vaporizer to implement a particular "thermal profile" or correlates or associates such a thermal profile with the vaporizable material and/or cartridge containing the vaporizable material.

Figure 3A:
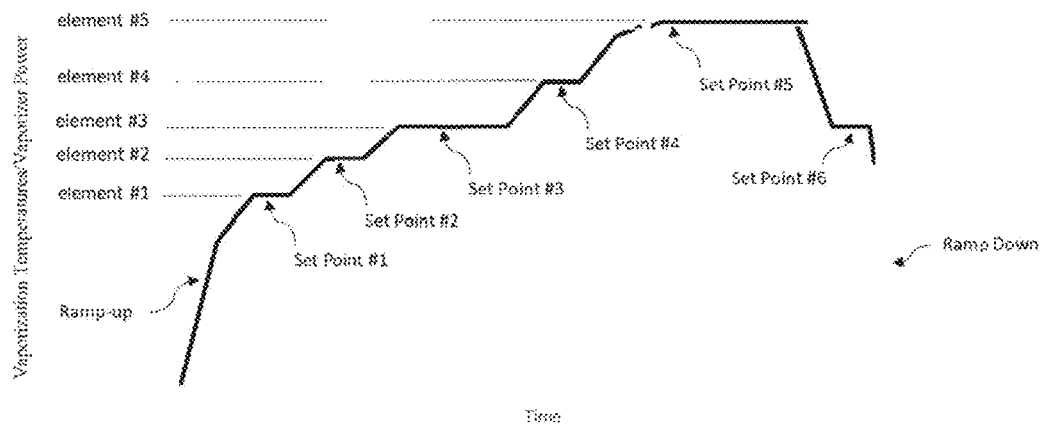
FIGS. 3A-3B illustrates two exemplary thermal profiles comprising a plurality of set points that are graphed on the vertical axis against vaporization temperatures of selected constituent elements of a vaporizable material and on the horizontal axis against time associated with an end-user inhalation of vaporized material from the vaporizer.
Figure 3B:
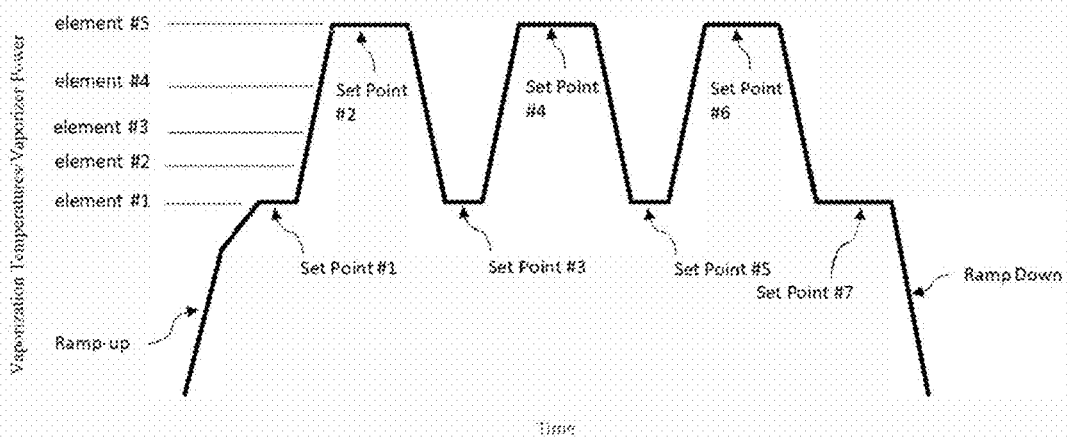

As illustrated in FIGS. 3A-3B and previously summarized, a "thermal profile" as used herein refers to a heating profile for a vaporization heating cycle that is associated with generating an aerosol or vapor dose for inhalation (e.g., draw or puff) by a user and is defined by a plurality "set points." A "set point" as used herein is defined by both (i) a power and/or temperature setting (e.g., Temp1, Temp2, Temp3, Temp4, Temp5, etc.) and (ii) a specified duration of time (e.g., T1, T2, T3, T4, T5, etc.) associated with that setting. A "set point" is distinct or different from the temperature/power and transient time associated with the heating ramp-up or ramp-down profiles of the vaporizer.

The different set points that define the thermal profile allow the different constituents elements of the vaporizable material to vaporize for set period of time and at a set temperature (or temperature range) and thereby control the composition of the vapor or aerosol generated from the vaporized material and inhaled by the consumer. Implementing a thermal profile to vaporize a material is capable of improving efficacy and consumer satisfaction (while also mitigating against potentially undesirable, less than optical, or unhealthy aerosol components), by more selectively controlling the mix of constituent elements of the vaporizable material that are ultimately contained within an aerosol or vapor dose of the vaporized material that is inhaled by the user. This is so because the vaporized amount of any given component element of vaporizable material is dependent on the particular element's vaporization temperature and the duration that the element is heated at or above its vaporization temperature. Since each element of a vaporizable material may contribute to a desired pharmacological, pharmakinetic, flavor, or other attribute of the vaporized material, employing a thermal profile specific to the vaporizable material to control the vaporization conditions can significantly impact efficacy and consumer satisfaction.

FIG. 3A illustrates one example of a representative thermal profile in accordance with the subject matter disclosed herein. The thermal profile illustrated in FIG. 3A is comprised of five (5) consecutively escalating set points that generally correspond to the vaporization temperatures of various selected constituent elements #1 through #5 identified on the vertical axis of the illustrated graph and one set point (#6) on a deescalating portion of the thermal profile that corresponds with the vaporization temperature of constituent element #3. Thus, six (6) set points define the thermal profile illustrated in FIG. 3A.

FIG. 3B illustrates another example of a representative thermal profile in accordance with the subject matter disclosed herein. The thermal profile illustrated in FIG. 3B is comprised seven (7) set points comprised of two repeating set points that correspond with the vaporization temperature of element #1 and element #5 with the intermediate vaporization temperatures of elements #2-4 residing there between.

While a thermal profile is defined as noted above by a plurality of set points, a "heating and cooling profile" that employs a thermal profile, as used in this disclosure, is defined by both the thermal profile and the transient heating and cooling profiles that occur from one steady state (e.g., set point #1) to another steady (e.g., set point #2). Thus, the line graphs illustrated in FIGS. 3A and 3B, when viewed in their entirety, illustrate a heating and cooling profile that is defined in part by the thermal profile set points and the transient heating and cooling profiles of the heating element 320. The transient heating and cooling profiles are generally determined by the inherent thermodynamic properties of the heater 320 and the amount and rate of power being transferred to the heater 320. Thus, the transient heating and cooling profiles can be engineered and/or programmed to perform in an intended or desired manner to achieve an overall heating and cooling profile.

Figure 3C:
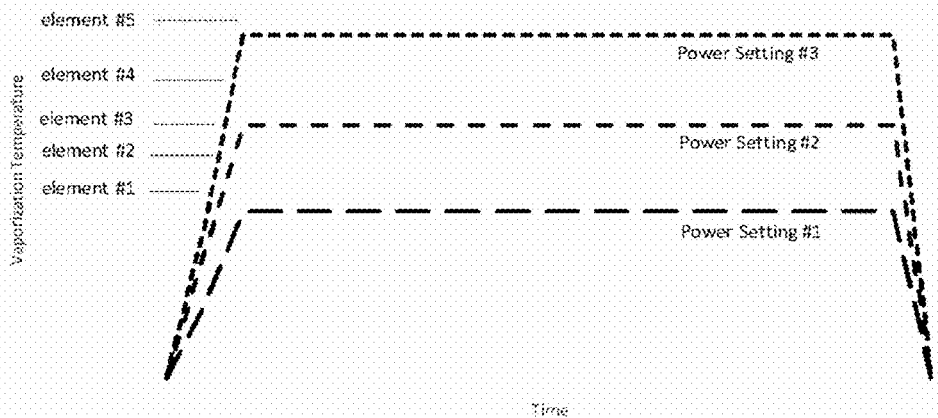
FIG. 3C illustrates a conventional vaporizer wherein a single temperature of power setting is used to vaporize the constituent elements of a vaporizable material. For purposes of illustration three different temperature/power settings are graphed on the vertical axis against the vaporization temperatures of the selected constituent elements of the vaporizable material illustrated in FIGS. 3A-3B and on the horizontal axis against time associated with an end-user inhalation of vaporized material from the vaporizer.

In contrast to FIGS. 3A and 3B, FIG. 3C illustrates a heating and cooling profile of a conventional vaporizer that includes a thermal control that pre-selects or otherwise allows a user to select a single temperature or power setting for vaporization of vaporizable material to generate a dose for inhalation by the user. Set points #1-#3 are each representative of a single temperature or power setting. The user often times selects the temperature or power setting that is insufficient or too elevated such that vaporizable material goes un-vaporized or is vaporized unnecessarily at a less than optimal temperature. Thus, as illustrated in FIG. 3C, a low temperature/power setting selection (Temp/Power Setting #1) is insufficient to vaporize elements #1-#5, the mid-temperature/power setting (Temp/Power Setting #2) while capable of vaporizing elements #1-#3, is insufficient to vaporize elements #4 and #5, and the high temperature/power setting selection (Temp/Power Setting #3) while capable of vaporizing all or almost all of elements #1-#5, the relatively high setting indiscriminately vaporizes those elements and does so at a temperature greater than needed (or necessarily optimal) for elements #1-#4.

It should be understood that the thermal profiles and the heating and cooling profile defined thereby that are illustrated in FIGS. 3A and 3B are merely representative. Thus, the number of set points and their relative temperature and duration may be modified or customized for a particular vaporizable material to effectuate a desired vaporized material composition for each inhalation or series of inhalations. Thus, for example, the thermal profile illustrated in FIG. 3A may extend over two or more inhalations with the first inhalation extending to Set Point #3 and the second inhalation extending from Set Point #3 to Set Point #6. Alternatively, with respect to the thermal profile illustrated in FIG. 3B, each inhalation may extend from Set Point #1 to Set Point #2 to Set Point #1. It should be understood, that the transient heating and cooling profiles may be also engineered and/or programed to effectuate or implement an overall heating and cooling profile for a particular vaporizable material and vaporizer that is capable of generating an aerosol or vapor composition that is more effective and/or satisfying to the consumer.

Further, it should be understood, that while each set point in the thermal profiles illustrated in FIGS. 3A and 3B are illustrated as corresponding to a specific temperature, the specified or programed temperature for a thermal profile may not be exactly achieved by the vaporizer 100. Thus, one of ordinary skill in the art would understand that a particular specified temperature in a thermal profile encompasses a reasonable expected range of values consistent with the capability of the particular vaporizer utilized. Thus, for example, if a vaporizer is capable of achieving a set point temperature of 350 degrees Fahrenheit with precision of +/−3 degrees Fahrenheit then a specified set point of 350 degrees Fahrenheit would encompass a range of 347-353 degrees Fahrenheit.

Similarly, a set point temperature may be defined by a temperature range as opposed to a single temperature. For example, a particular set point may be defined by a temperature range between 340-350 degrees Fahrenheit for a period of 0.5 seconds. Further, a set point may be defined by a power setting or range thereof and a duration of time as opposed to a temperature setting or range thereof and a duration of time. Thus for example, a set point may be defined by the number of watts (or other indicia or measurement of power) or a wattage range and a duration of time (e.g., 0.5 seconds). Power and temperature, in the context of defining a thermal profile, therefore can be considered proxies for one another. Other proxies for power and/or temperature may be used and/or substituted therefore in defining a thermal profile set point.

Further, it should be understood that although there are different inhaling techniques, a single inhalation typically occurs in a very short time period, typically from less than a second to approximately four (4) seconds in duration. During that time the consumer is primarily focused on inhaling vaporized materials. Accordingly, even if the consumer had knowledge of each constituent element contained in the vaporizable material, understood the vaporization temperature of each of those constituent elements, and developed a desired thermal profile for vaporizing the vaporizable material consistent with this knowledge, the consumer would have great difficulty to implement a thermal profile or do it with any precision or accuracy using the user controls for such conventional vaporizers. Moreover, users are typically not provided sufficient information on the physical and chemical properties of the component elements of the vaporizable material and the interrelationship between those constituent elements and even if user's were to provide them may not sufficiently understand them to effectuate a satisfactory thermal profile.

Thus, the vaporizer 100 disclosed herein has the capability of automating thermal profile control through the use of a thermal profile recipe code 350 associated with the vaporizable material. As illustrated in FIG. 1C, the controller 220 of the vaporizer 100 implements a heating and cooling profile defined in part by the thermal profiles consistent with and in accordance to the thermal profile recipe code 350. The thermal profile recipe code 350 may also dictate, at least to some degree, the transient heating and cooling profiles of the heating and cooling profile by controlling or otherwise dictating the rate and/or amount of power the controller 220 is allowed to transfer to the heater 320.

The thermal profile recipe code 350 may be implemented in hardware and/or software to effectuate a desired thermal profile (and more broadly the heating and cooling profile defined thereby) via instructions to the controller 220 relating to the regulation of power to the heater 320. The thermal profile recipe code may be embodied on an electronic circuit, such as integrated circuit or microchip or a memory component (e.g., DRAM, FRAM, RFID, NFC tag, etc.) Thus, for example, the thermal profile recipe code 350 may be a thermal profile program (or compilation of programs) comprising an executable set of instructions that when processed by the controller 220 effectuates the thermal profile. Alternatively, the thermal profile recipe code 350 may be a thermal profile identifier that corresponds to a thermal profile that is pre-programmed and/or stored in the vaporizer memory 290, such that for example when the cartridge 300 is engaged with the vaporizer body 200, the thermal profile identifier is read and used to select or identify the appropriate thermal profile program stored in the vaporizer memory 290.

The thermal profile information encoded in the thermal profile recipe code 350 may comprise a single or multiple thermal profiles (or thermal profile identifiers), the implementation of later may depend on the use conditions. Thus, for example, varied thermal profiles may be implemented based on the number of inhalations and/or the length of those inhalations. A particular thermal profile (or thermal profile identifier) may be encoded for use for a single slow long draw or inhalation, while one or more different thermal profiles (or thermal profile identifier) may be encoded for use for multiple quick short draws or inhalations, either individually or across a plurality of those inhalations. Hence, the thermal profile information encoded on the thermal profile code 350 may be correlated with variations in the actual or anticipated use of the vaporizer 100. Use-specific or adapted thermal profiles can be implemented in a variety of ways. For example, via pre-programing the thermal profile information and associating that information with specific use conditions. Those use conditions may be known, selected, or provided by the end-user or derived or learned from user data.

Alternatively, a particular thermal profile may be adaptively modified via feed-back or adaptive control data, user interface inputs, or sensor data. The vaporizer sensors 260 inputs 270 may be utilized by the controller 220 in effectuating the thermal profile. Thus, for example ambient temperature and pressure sensor may provide data on the reservoir temperature that allows the controller to better regulate the power to the heater 320 to more accurately effectuate the desired thermal profile. Thus, it is contemplated that the controller 220 may utilize feed-back or adaptive control to effectuate a thermal profile. The adaptive control may include, for example, user interface inputs 270 that facilitate user modification or adjustment of the thermal profile, e.g., adjusting the thermal profile temperature upward or downward, compressing or expanding the length of the thermal profile, or selecting an option whereby the thermal profile is to be applied by the controller over a specified series of inhalations or draws (e.g., over 1, 2, 3, or 4 etc. draws), escalating or deescalating power to the heater 320, increasing or decreasing duration and or temperature of one or more set point, removing or adding set points, or any combination thereof.

The thermal profile recipe code 350 may be comprised of a volatile or non-volatile memory component, wherein a thermal profile program (or thermal profile identifier) is encoded, together with circuitry capable of communicating the encoded thermal profile information either directly or indirectly to the controller 220. Communication of the encoded thermal profile information may be via the electrical circuit created between the electrical contacts 271a-271c on the vaporizer body 200 and the electrical contacts 371a-371c on the cartridge 300. Alternatively, the thermal profile information may be stored in an near field communication ("NFC") or radio frequency identification ("RFID") tag or other memory tag, located on the vaporizer cartridge 300 and read by the wireless circuit 280 or other suitably adapted reader on the vaporizer body 200 (or in communication with the vaporizer) where once read is either stored into memory 290 for later use (and/or directly used) to instruct the controller 220 to effectuate the desired thermal profile upon use or inhalation of the vaporizer 100.

Activation and deactivation of the vaporizer 100 may be achieved manually via a button, shaking, audible command, or by sensing air flow, pressure drop, or capacitive changes resulting from the user inhaling or interacting with the mouthpiece 340 of the vaporizer 100. The duration of the activation may be coextensive with, exceed or be less than the duration of the thermal profile.

As discussed above, conventional vaporizers and sourcing models do not take into account implementing a heating profile that corresponds to a thermal profile associated with a particular vaporizable material. Rather, there is a long drawn out process that manufacturers of vaporizable material and manufacturers of vaporizers go through to source a vaporizer for a particular vaporizable material to market. The process involves numerous meetings and often times physical modifications of the vaporizer and ultimately leaves the end-user to blindly adjust the temperature or power setting of the vaporizer through a trial and error approach that is fundamentally incapable of implementing a thermal profile for the particular vaporizable material. Since differences in composition, chemistry, viscosity, color, flavor, manufacturing methods, and/or environmental conditionals may impact the desired or optimal vaporization of a vaporizable material, the disclosure here contemplates that those most knowledgeable of the vaporizable material (i.e., the vaporizable material experts) are in a preferred positioned of knowledge to define a thermal profile for that vaporizable material and are also vested in achieving the highest consumer satisfaction.

The thermal profiling defining process may include the following representative steps. The vaporizer device manufacturer provides a programmable vaporizer unit that is capable of programing and recording a thermal profile, testing, and adjusting or optimizing the thermal profile for a particular vaporizable material. This step may be aided with the user of an external computing device 700/800 depicted in FIG. 2A-2B that is capable of depicting or otherwise presenting, adjusting, and documenting the thermal profile and the overall heating and cooling profile of the vaporizer 100. Through the use of the programmable vaporizer unit, the manufacturer or supplier of the vaporizable material determines (through testing or otherwise) the desired or optimal thermal profile for its vaporizable material in the context of a heating and cooling profile that takes into account transient heating and cooling profiles associated with the vaporizer 100. It is contemplated that this process can be achieved during a single meeting between the manufacturer of the vaporizer and the manufacturer of the vaporizable material. Once defined, the thermal profile is documented so that it can be encoded to a memory component of the thermal profile recipe code 350. The thermal profile is then associated with the vaporizable material during the packaging process of the cartridge 300 by way of including a corresponding thermal profile recipe code 350 on (or in) the cartridge 300. The cartridge 300 containing the vaporizable material and corresponding thermal profile recipe code 350 is then shipped to end-users for consumption. Once the end-users insert the cartridge 300 into the vaporizer body

200, the pre-programmed thermal recipe code 350 is automatically communicated to the vaporizer body 200 as previously described, which in response thereto implements a heating and cooling profile via the controller 220 in accordance with the thermal profile information encoded in the thermal profile recipe code 350. Each end-user, therefore, is capable of having a consistent and common vaporization experiences for a particular vaporizable material and vaporizer 100 without waste or frustration and with the full knowledge that the vaporizable material is being properly and safely consumed in the manner intended by the manufacturer/supplier of the vaporizable material.

Use data, including the types of products used over a period of time, duration between usage, buying frequency, usage rate, capacity of contents within a vaporization cartridge, usage habits, inhalation rate, duration of inhalation, user toleration, time of day, learned usage related to time or day or date, position of device, agitation of device, movement of device, environment, humidity, temperature, altitude, consumer input such as, user intent, height, weight, age, gender, body measurements, hobbies, interests, employment status, type of employment, preferred method of use, experience with vape devices, experience with specific contents, level of discretion, desired size of vaporization cloud, social application (such as performances, family events, etc.), taste preferences, correlation to meals, intensity of specific elements, battery life and/or a plurality of other factors can be tracked and stored in memory 290 and either retained therein or communicated to an external device 700 or 800.

The use data can be analyzed in connection with adapting, adjusting, or creating alternative or derivative thermal profiles from those originally defined and encoded on the thermal profile recipe code 350. These alternative or derivative thermal profiles can then be loaded into memory 290 of the vaporizer body 200 or vaporizer cartridge 300.

The use data can also inform, provide a platform for, enhance, or otherwise be used to support, create, or facilitate interactions between end-users, vaporizable material manufacturers, vaporizer device manufacturers, and/or others via social media, online or traditional marketing or communications. Additionally use data, may be provided to end-users so they can track or analyze usage of their vaporizers. The data may be presented as a dashboard summarizing selected use metrics, which can be communicated to the user directly via a suitable output or transmitted or otherwise communicated to an external device, such as the user's smart phone or computing device.

Further, when a vaporizer is prescribed or desired to be used in a predetermined manner, a scheduling system can push notifications to the end-user, a company, or medical advisor to prompt the timely use of a vaporizer. The scheduling system and/or schedule can be on specialized or generic application residing on an external device or server 700, 800 that is capable of communicating with the user directly, or via the vaporizer output 250 or another device such as a smart phone or pager. Alternatively the scheduling system and/or schedule can be programmed in the vaporizer memory 290 or encoded onto the thermal profile recipe code 350 on the cartridge 300 and provide notifications to the end-user directly via the vaporizer 100 and/or to the user's external device such as smart phone or watch. The scheduling system may notify or otherwise remind the user to use the vaporizer 100 to inhale a specific vaporizable material using a specific thermal profile at a specified time or frequency, which may be based on body metrics such as heart rate, blood pressure, cardiac rhythm, or other biological or physiological conditions or measurements that are known or obtained by the inputs 270 of the vaporizer 100, an external device 700/800 such as a smart phone or watch, or from the health records of the user. Notification or alerts can include audible, visual, vibration, and/or electronic notices that are communicated to the user via the vaporizer 100 or an external device 700 like a smart phone or watch or the like.

Figure 4:
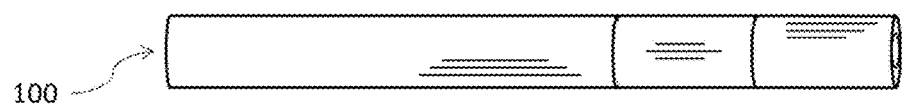
FIG. 4 illustrates a one-piece vaporizer form factor in which the vaporization body and vaporization cartridge are not adapted to being disengaged from one another by the user.

While the foregoing disclosure is described in the context of a two-piece vaporizer 100, it should be understood that the subject matter may be readily implemented in any vaporizer including a vaporizer 100' that does not use a detachable cartridge, such as that illustrated in FIG. 4. In such an implementation, for example, the components described in connection with FIGS. 1A-1C would be contained within the vaporizer 100'. The electrical circuitry, including that created by electrical contacts 271a-271c and 371a-371c may be substituted with hardwired circuit(s) or be part of an integrated circuit, ASIC or PCB that includes the controller, memory, communication circuitry (e.g., 220, 290, 280); input and output circuitry (including sensor circuitry) (e.g., 270, 250, 260); charging and power regulation circuitry (e.g., 230, 240); and thermal profile code 350, which may be part of the controller 220 or memory 290 or may remain as a separate component. The vaporizable material may be packaged with information for the user to select or download the thermal profile code 350 to the vaporizer device 100' or such information may be available from the vaporizable material manufacturer or third party website or database accessible by the user.

Further implementation examples of the foregoing are set forth below.

Implementation Examples

Figure 5:
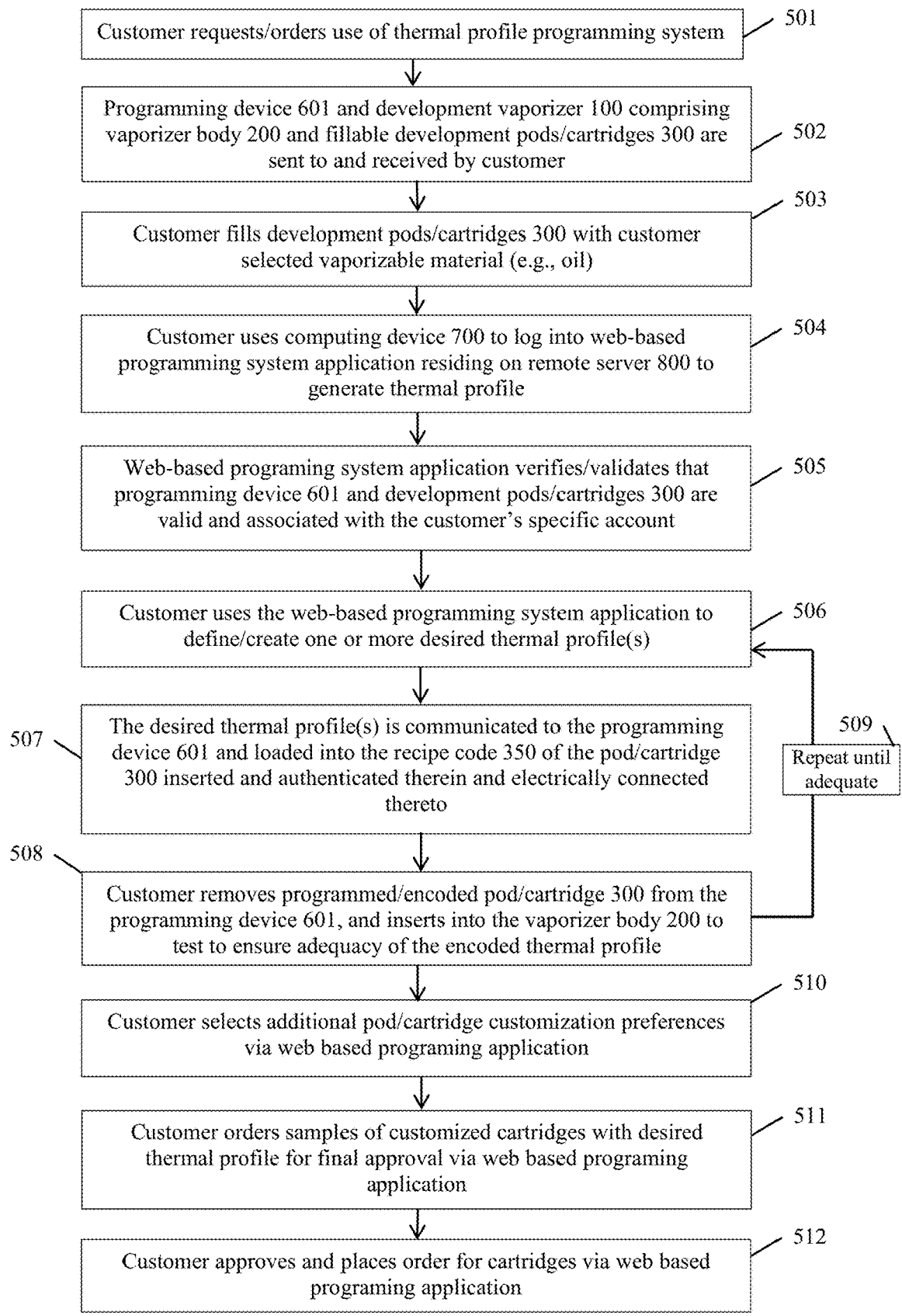
FIG. 5 illustrates a process flow diagram for programming vaporizer cartridges and implementation of various aspects of the subject matter disclosed herein.
Figure 6:
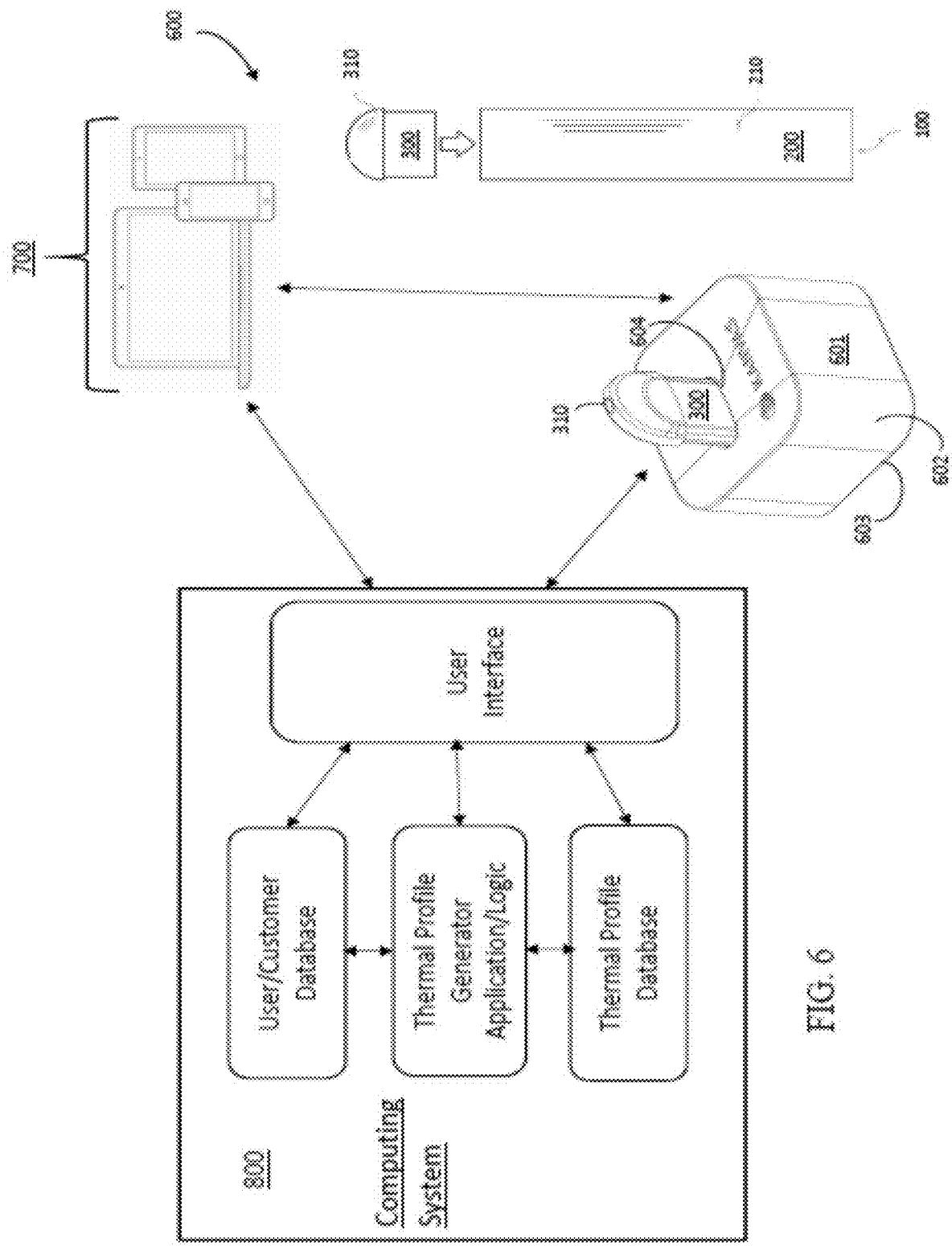
FIG. 6 is a diagram illustrating thermal profile programming system implementations.

A process that implements various aspects of the foregoing is set forth in the process flow diagram of FIG. 5. The process depicted in FIG. 5 may be performed using a programming system, such as the system 600 depicted in FIG. 6, which is generally comprised of a dedicated thermal profile programming device 601, a vaporizer 100 including one or more programmable vaporizer cartridges 300 (such as that illustrated in FIGS. 1A-1C), and the electronic computing device 700 and remote server 800 illustrated in FIGS. 2A-2B and described above. As illustrated in FIG. 6, the remote server 800 is basically a computing system that has a thermal profile generator application or logic, a user or customer database and a thermal profile database, and a user interface. The user interface is capable of interfacing and communicating with the programing device 601 directly and/or indirectly through computing device 700. The communication links (depicted by arrows in FIG. 6) between the system components 601, 700, and 800 may be wired and/or wireless. The user/customer database may contain information specific to user or customers, such as login information, thermal profile preferences, name and address, purchase history etc. The thermal profile database may contain information regarding thermal profile recipe correlation tables (such as that depicted in FIG. 10) or other information (e.g., thermal properties, activation temperatures, flavors, effects) by which a thermal profile recipe may be generated or selected by the thermal profile generator application or logic. The thermal profile generator application or logic can be software and/or hardware that considers the vaporizable material and user's input or preferences with reference to the vaporizer 100 heating properties and selects or generates a thermal profile recipe 350 in accordance therewith.

The programming device 601 illustrated in FIG. 6 is comprised of a housing 602 that includes a support base 603 that is configured to stand on a flat surface and a receptacle 604. Like the vaporizer body 200 described above, the cartridge receptacle 604 includes electrical contacts 271a-271c that are complimentary to the electrical contacts 371a-371c on the base of the cartridge 300 and configured to engage with each other when the vaporizer cartridge 300 is properly inserted into the receptacle 604 of the programming device 601. When the cartridge 300 is properly inserted in the receptacle 604, the programming device can communicate with the cartridge 300 through the complementary electrical contacts 271a-271c and 371a-371c and program/encode the recipe code 350 of the cartridge with the desired thermal profile.

Figure 7:
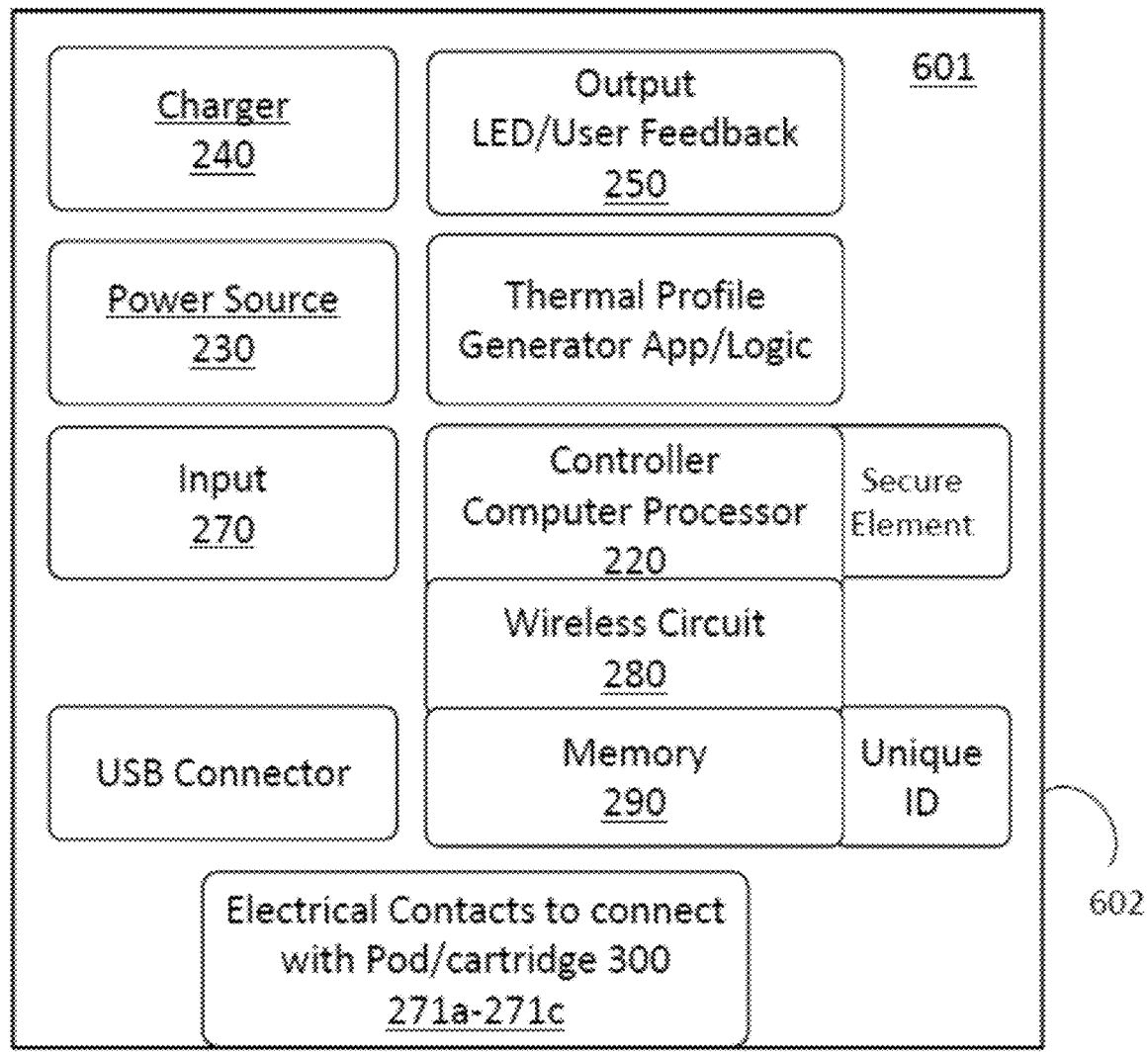
FIG. 7 is a block diagram of components that may be contained within the housing of a thermal profile programming device, such as the one depicted in FIG. 6.

As illustrated in the block diagram of FIG. 7, the programming device 601 includes components that correspond to the vaporizer body 200 described above. Contained within the housing 602 of the programing device 601 are electrical components comprised of controller 220, wireless circuit 280, memory 290, power source 230, charger 240, output 250, and inputs 270, USB connector to facilitate charging and wired communication and the electrical contacts 271a-271c to connect with the cartridge 300, which operate generally in the manner previously described vis-à-vis vaporizer body 200 to facilitate the receipt and communication of the user selected/defined thermal profile (as described in more detail below) and encodes/programs the generated or selected thermal profile onto the recipe code 350 of the cartridge 300 connected thereto via the complementary electrical contacts 271a-271c and 371a-371c that are engaged with one another when the cartridge 300 is seated within the receptacle 604 of the programming device 601. Thus, as illustrated in FIG. 6, the programming device may function as a communication device to receive and program the recipe code 350 of the cartridge 300 with a particular thermal profile that is communicated to the programming device 601, directly from a computing system 800 that generated it or indirectly through another computer or electronic device 700. The thermal profile information and other communications to and from the programing device 601, may be encrypted in transit (and potentially also at rest in memory) and decoded by the programming device 601 prior to being encoded onto the recipe code 350. Alternatively, the programing device 601 may encode the thermal profile onto the recipe code 350 in an encrypted form, in such an implementation the thermal profile could be decrypted in operation by the vaporizer 100 when used. To facilitate encryption and/or encryption decoding, the controller 250 on the programming device 601 and/or vaporizer 100 may include a secure element.

Further as illustrated in FIG. 7, the programming device 601 itself may further include a thermal profile generator application or logic component and the memory 290 may include the user and/or thermal profile databases used to generate or select a thermal profile for encoding onto the recipe code 350. User interaction with the programming device 601 could be direct via a local computer 700 or a standalone keyboard and monitor via a wired connections via the USB connector or a wireless connection via the wireless circuit 280. Alternatively, user interaction with the programming device could be through the computing system 800, which the user can interface with using a local computer 700. In this manner, the user or customer could interact with the programing device 601 and generate or select a thermal profile for programming or encoding onto the cartridge 300 without having to interact therefore with a remote server 800 or a local computer 700. The programming device 601, would thus be stand-alone system that could be used by the customer with or without a remote server 800 and/or local computer 700. To the extent external validation of one or more of the programming system 600 components is required or desired, the programming device 601 could communicate directly or indirectly with a remote server 800. Similarly, to the extent external thermal profile data and or user customer data or other resources are required or desired that exist outside the programming device 601, the programming device 601 could communicate directly or indirectly with a remote server 800 to obtain such resources or support.

Thus, it should be understood that the programming system depicted in FIG. 6 represents various implementations. The programming device 601 in one implementation depicted therein could be a standalone programming system or could rely or be supported, in one or more various aspects, through communications with a remote computing system 800 and/or one or more local computers 700.

A further implementation may include the same components as depicted in FIG. 6, yet the programming device 601 and cartridge 300 may be in a location that is different from the location of a person providing the information to generate a thermal profile.

Figure 9:
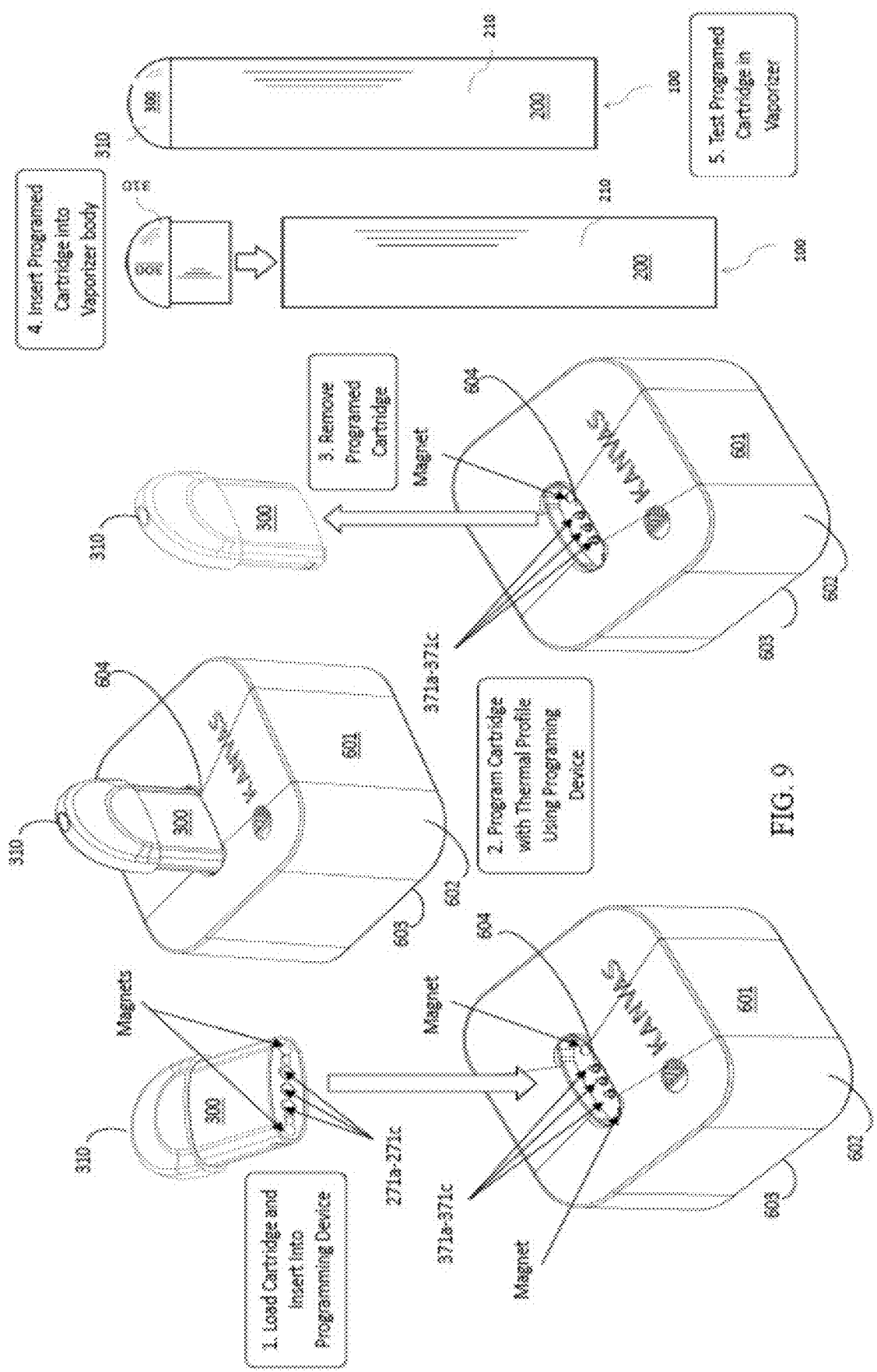
FIG. 9 is an illustration of steps involved in selection of a customized thermal profile in accordance with the implementations described herein and the process flow diagram of FIG. 5 and programing system described herein.

With reference to the process flow diagram of FIG. 5 and the illustrations set forth in FIG. 9, the customer can initiate the process by using the electronic device 700 to communicate (e.g., via the internet or otherwise) with the remote server or computing system 800 via the user interface an interact with a web-based software programing system application residing on the remote server 800 to create a customer account (e.g., user name, password, address, payment method, etc.) via the web-based application and request use of the thermal programming system (step 501). Customer account information any other information provided by the customer would be stored on the user/customer database for later use and to track account history.

In response to the customer's request, the programming device 601 and a development vaporizer 100, which is comprised of a vaporizer body 200 and one or more detachable and interchangeable user fillable development pods/cartridges 300 are sent to the requesting customer (step 502).

The development vaporizer 100 is preferably selected to correspond to customer preference. Some customers may require or use one type/brand of vaporizers and other customers may require or use another type/brand of vaporizer that performs differently. It is contemplated therefore that the development vaporizer 100 sent to the customer perform, from a consumer standpoint, in the same manner as, or otherwise in accordance with, the vaporizer 100 that the customer ultimately sells or markets to end users and ideally would be identical thereto. Upon receipt, the customer fills the development pods/cartridges 300 with the customer's vaporizable material (e.g., oil) (step 503).

The customer uses computing/electronic device 700 to log into the programming system application residing on remote server 800 to generate thermal profile (step 504). Before allowing the user to generate a thermal profile, the web-based programing system application may verify that the programming device 601 and/or development pods/cartridges 300 are valid and that they are associated with the customer's specific account (step 505).

The validation process can be part of a customer sign-in-process to the web-based application and may be accomplished by reading and validating a unique identifier preloaded onto the memory 290 of programming device 601 and/or cartridge 300. For example, the user may use the electronic device 700 to read the unique identification information pre-loaded onto the programming device 601 and/or cartridge 300 and send or input that information into the web-based programming system application which upon validation sends a code that unlocks the programming device. The unlock code can be sent or communicated directly to the programming device and/or through the customers electronic device 700 via a wired or wireless communication link. Once unlocked, using electronic device 700 to communicate with remote server 800, the customer interacts with the web-based programming system application to define/create one or more desired thermal profiles (step 506).

The process by which such thermal profiles may be created is described below in more detail. Once the desired thermal profile is defined/created, it is communicated to the programming device 601 and loaded into the recipe code 350 of the pod/cartridge 300 that is inserted therein and electrically connected thereto (step 507).

The communication of the generated thermal profile from the remote server 800 to the programming device 601 may be through any suitable communication link (e.g., wireless or wired). For example, the communication of the generated thermal profile from the remote server 800 to the programming device 601 may be directly communicated to the programming device in a manner independent of the electronic device 700 or may be communicated through or by the electronic device 700 to the programming device 601. Once the pod/cartridge 300 is programmed with the desired thermal profile, the customer can remove the programmed/encoded pod/cartridge 300 from the programming device 601 and inserts it into the vaporizer body 200 to test it (step 508). The testing process may be varied, and may be comprised of objective and subjective factors. For example, a customer may actually consume the vaporizable material and based on the customer's experience deem it adequate or inadequate. Alternatively, the testing process may be comprised of vapor samples that are tested for compositions, smell, flavor, and effect, or some combination thereof.

The customer can adjust the thermal profile by repeating the steps until the perfect or suitable thermal profile is obtained (step 509).

In addition, the entire process can be repeated for different customer vaporizable material with each thermal profile selected being associated by the programming system application with the customer account so that the customer can have a historical log of its thermal profiles for later reference and use as needed. Once a thermal profile for a particular vaporizable material is settled upon, the programming system application may query the customer for additional information or preferences to customize production of its cartridges (step 510). For example, the customer may be queried as to physical color or branding or art work it wants on the cartridges, or whether it wants its pod/cartridges 300 to be encoded to create specific outputs 250 such one or more optical (e.g., LEDs, displays, etc.), tactile (e.g., vibrational, etc.), or sonic (e.g., piezoelectric, etc.) feedbacks as previously described. as customized LED or haptic feedback control settings. FIG. 8K depicts a screen shot of an implementation of a web based programming system software that queries the user for feedback preferences.

The customer can then place orders via the web-based programming system application for sample cartridges 300 that are pre-programmed with the customer's selected thermal profile and other output settings and manufactured to the customer's physical specification to include the desired art work and color (step 511) and once approved can place non-sample orders through the application, which upon received are manufactured and sent to the customer for use (step 512).

Figure 8A:
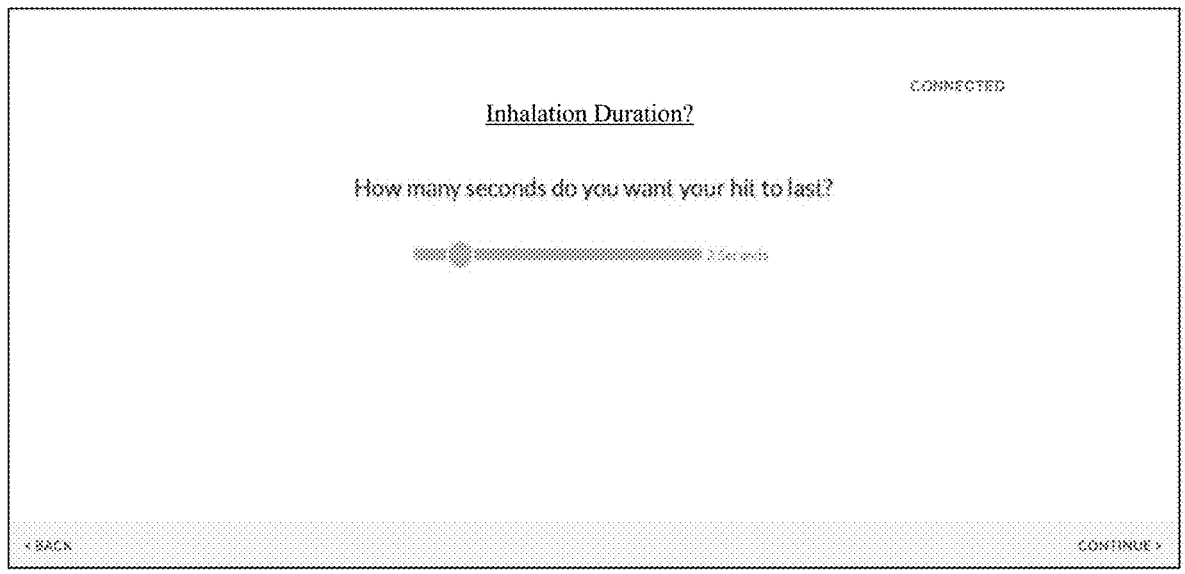
FIGS. 8A-8N are representative screen shots of a web-based programming system application that queries users/customers or users and in response to those queries generates or a customized thermal profile that is encoded on vaporizer cartridges provided to the customer or user in accordance with the customer or user preferences.
Figure 8B:
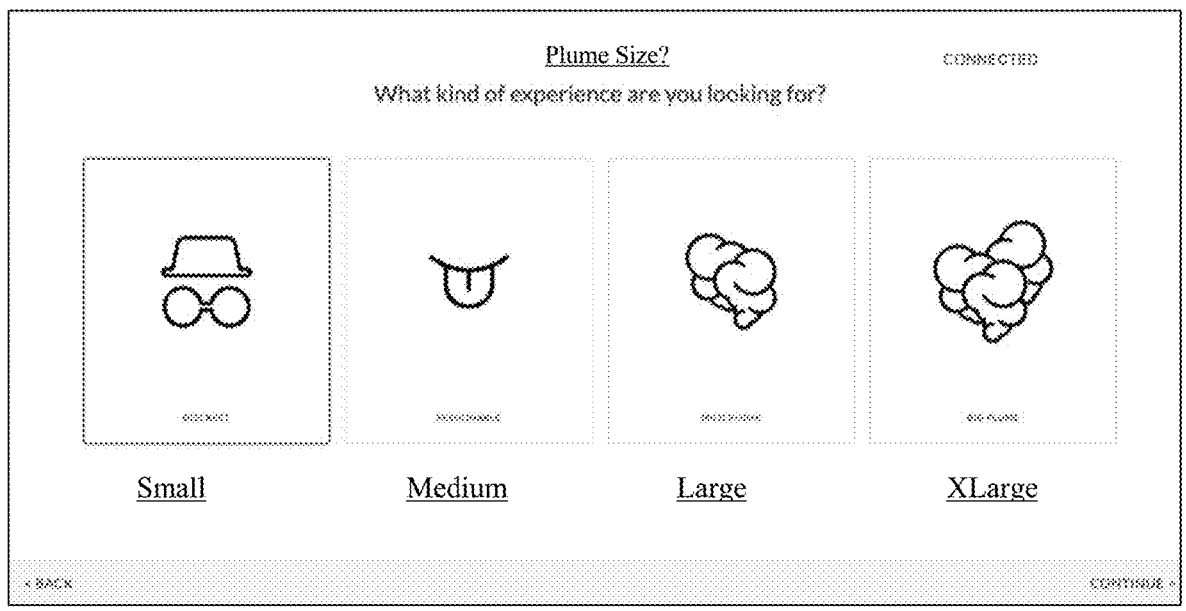
Figures 8C, 8D:
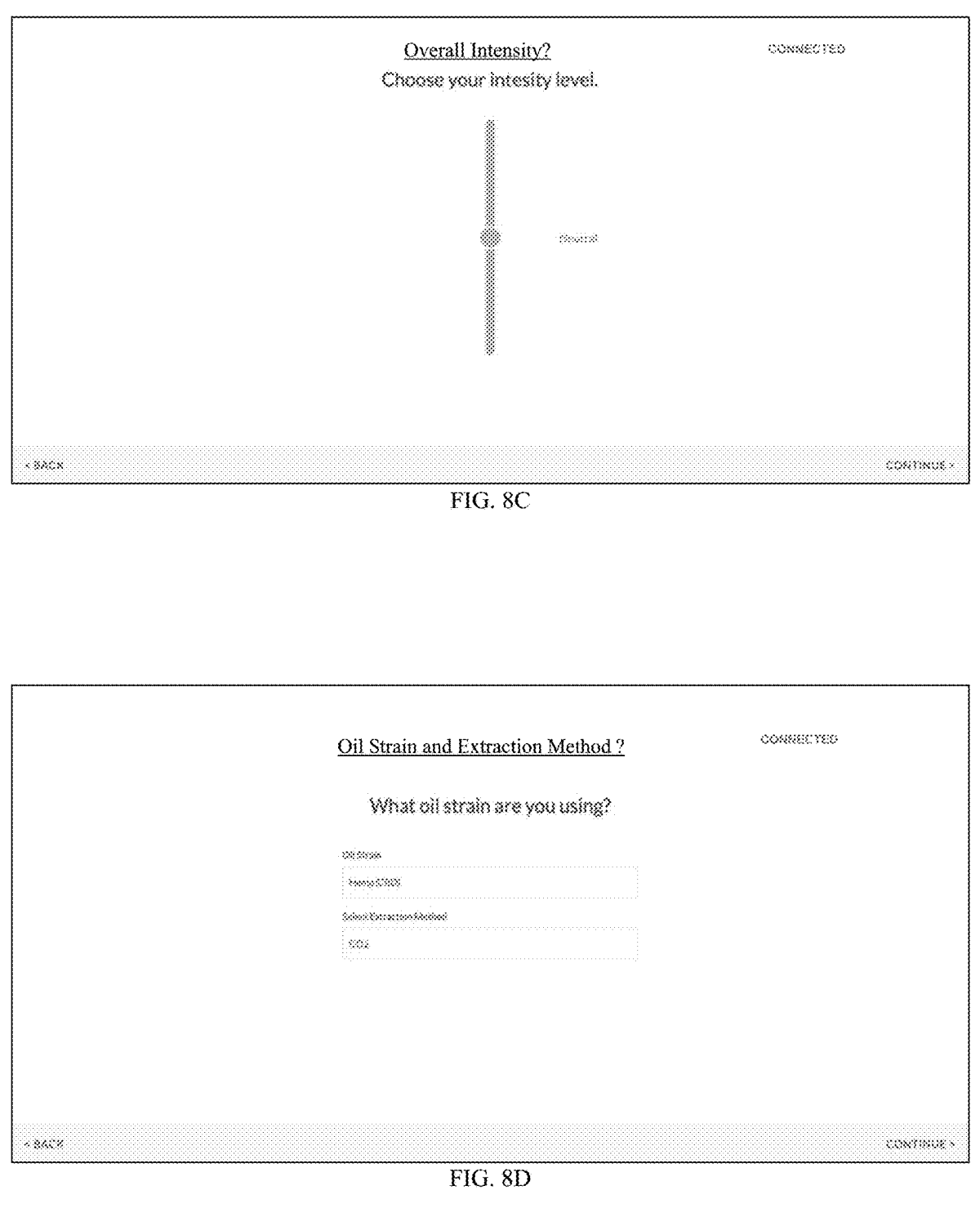
Figure 8E:
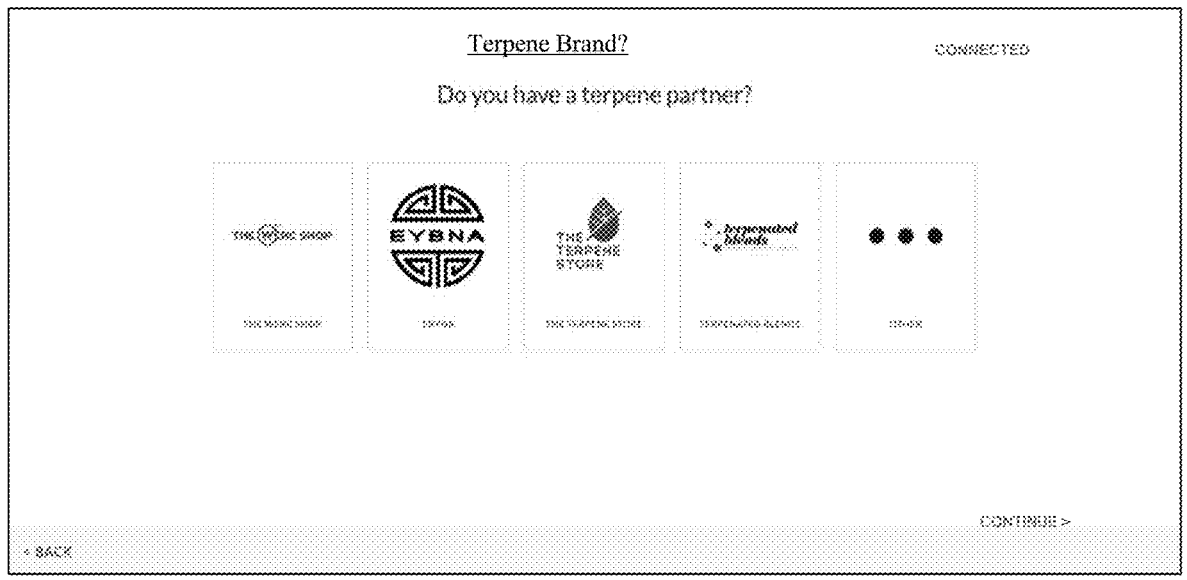
Figure 8F:
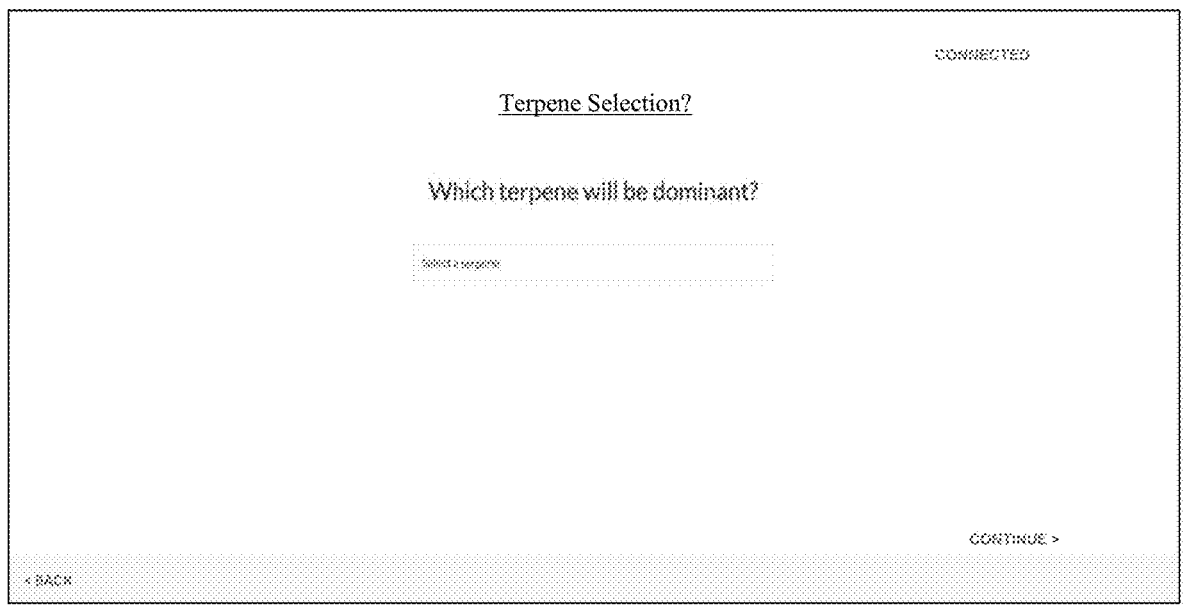
Figures 8G, 8H:
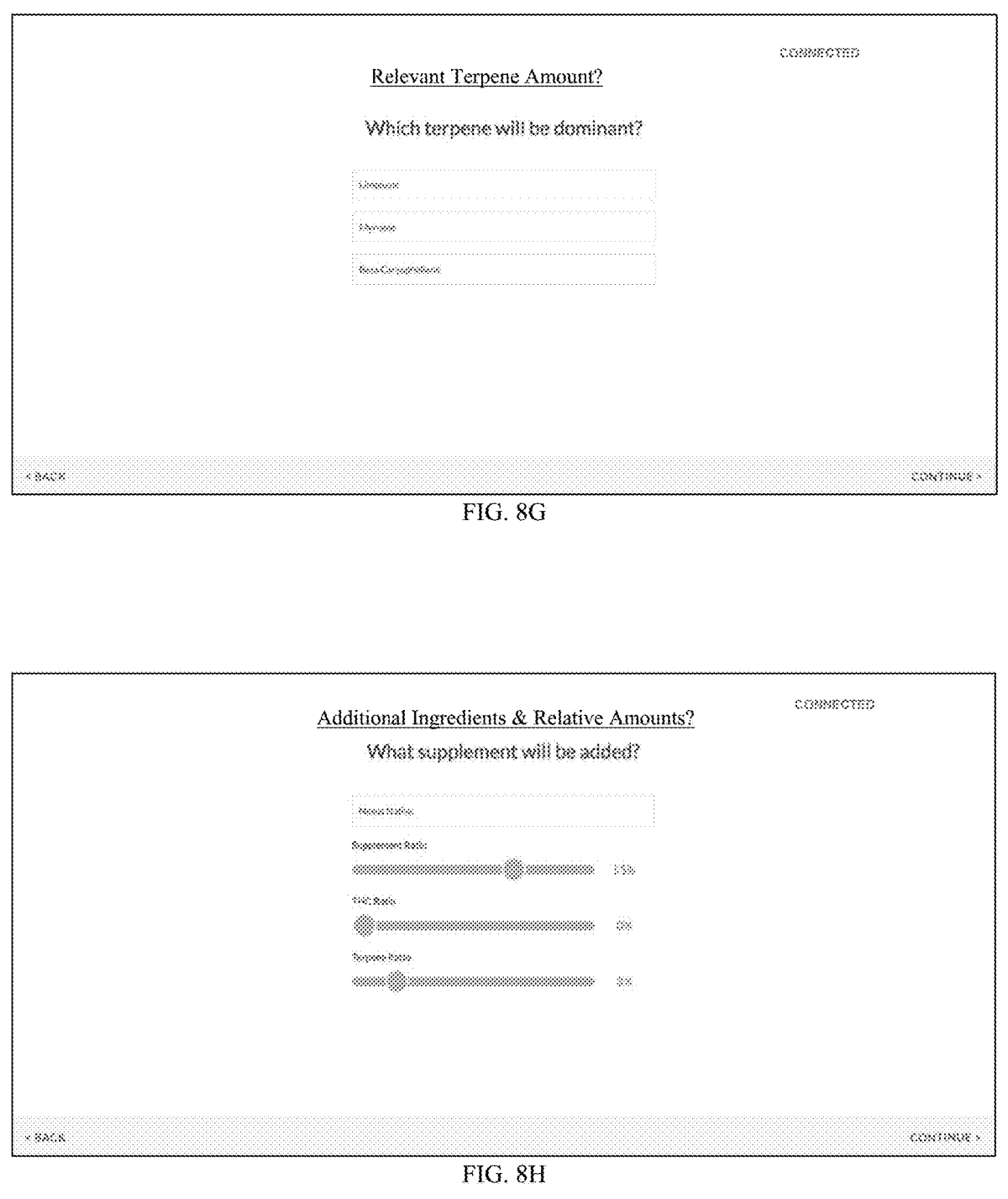
Figure 8K:
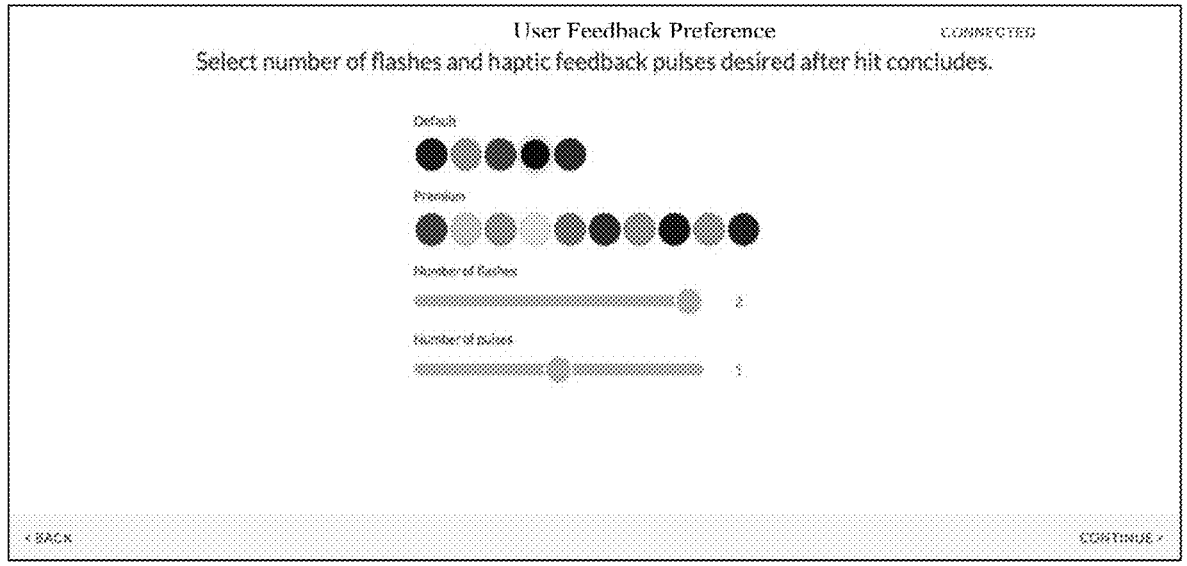
Figure 8L:
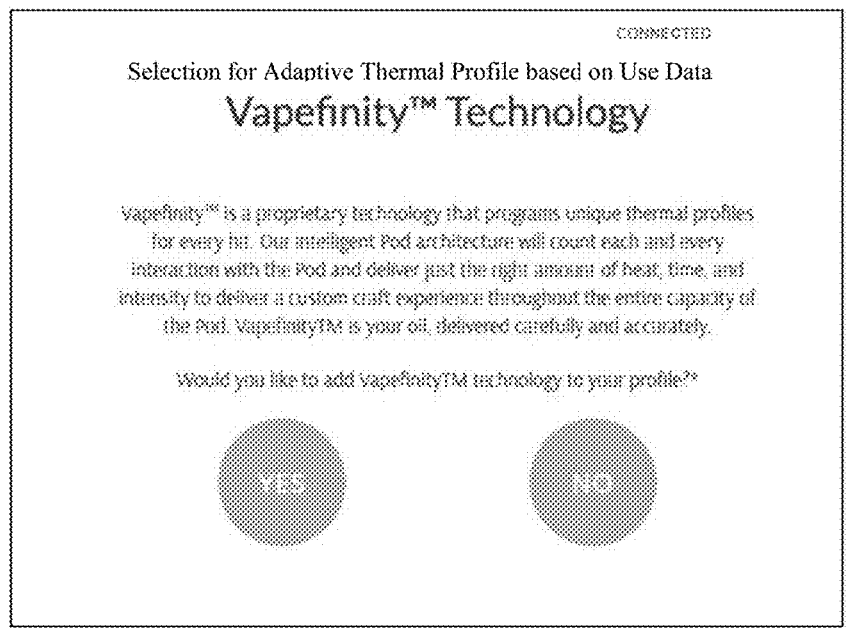
Figure 8M:
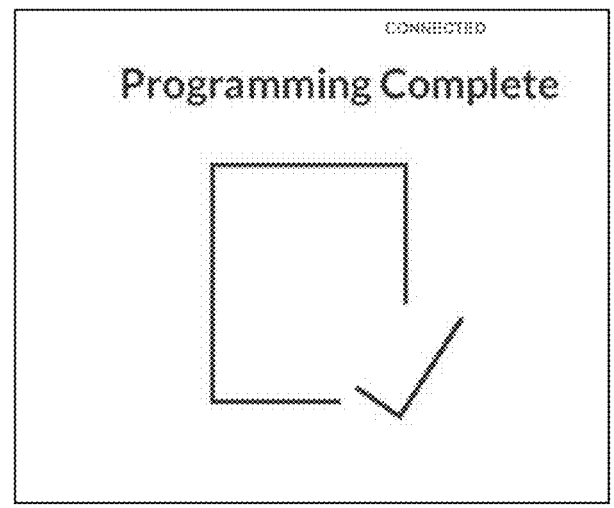
Figure 8N:
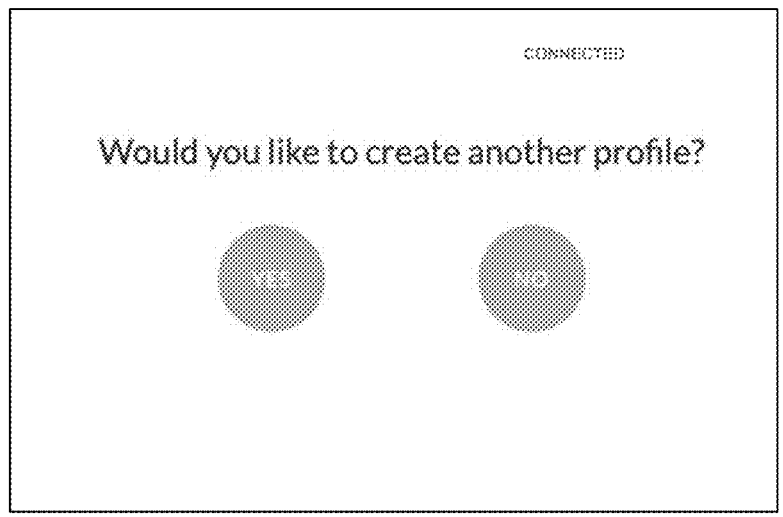

FIG. 8M depicts a screen shot of an implementation of a web based programming system software that informs the user that the programming of the pod/cartridge is complete (in accordance with step 507) and can be used also to inform the customer that customer's order is complete in accordance with steps 511 and/or 512), whereas the screen shot depicted in FIG. 8N provides the customer the option of creating another thermal profile in accordance with steps 506-508. Customer information, such as that illustrated in the screen shot depicted in FIG. 8I, may be presented and obtained from the customer at the beginning of the process, as part of the customer initiation process, in the middle of the process as part of the component validation process (step 505), or at the end of the process as part of the ordering process (steps 510-512).

The foregoing is an illustrative implementation. As illustrated in FIG. 6, it is contemplated, for example, that the programming device 601 may communicate directly with a remote server 800 without a local computer 700 to unlock the programing device by sending the unique identifier to the remote server 800 and receive the thermal profile directly therefrom and then encode the thermal profile onto the cartridge 300. The customer may initiate this process by connecting (wirelessly or via a wired connection bias the USB connector on the programming device) a monitor and/or keyboard, a tablet, or smart phone to the programming device 601 to interact or communicate with the remote server 800 to unlock and program the thermal profile. Further, it is contemplated that the programming device 601 may be self-contained such that the customer or user simply connects to the device 601 via an interface such as a monitor or keyboard and the programming device 601 without reliance on a remote computing system 800 and/or local computer generates or selects a thermal profile using an internal thermal profile generator application or logic and internal user/customer and/or thermal profile databases housed within the programming device 601.

With reference to FIG. 9, the left most image in FIG. 9 is a depiction of the process where after loading the cartridge 300 with the customer's vaporizable material, the customer inserts the loaded cartridge 300 into the receptacle 604 of the programing device 601 in accordance with step 503 of FIG. 5. The image in FIG. 9 second from the left is a depiction of the cartridge 300 been inserted into the receptacle 604 of the programing device 601 for programming the cartridge 300 with thermal profile. The image at the center of FIG. 9 is a depiction of the cartridge 300 been removed from the receptacle 604 of the programing device 601 after the programming process of the cartridge 300 is complete. The image in FIG. 9 second from the right is a depiction of the process where after the cartridge 300 been programmed with thermal profile, the customer inserts the programmed cartridge 300 into the vaporizer body 200. The right most image in FIG. 9 is a depiction of the cartridge 300 been inserted into the vaporizer body 200 and a test of the programmed cartridge 300 can be performed.

As previously described and as illustrated in the screen shots depicted in FIGS. 8A-8N, the implementation process of a heating and thermal profile can be automated via a computerized software application, which is programmed to generate a best fit thermal profile for a particular vaporizer device 100 that is in accord with the desired user experience and vaporizable material. Through the user interface electronic device 700, the web based programming system application residing on the remote server 800 presents the user with a series of queries relating to the desired user experience and the nature of the vaporizable material.

With reference to the screen shots depicted in FIGS. 8A-8C, experience/use related questions may, by way of example, include questions directed to: (1) inhalation duration (FIG. 8A), (2) desired level (e.g., degree, amount, or intensity) of a particular flavor, the vaporization of a particular ingredient, pharmacological effect, or combined overall intensity (FIG. 8C), and (3) the desired plume size or volume of vaporized material (e.g., small, medium, large or extra-large) (FIG. 8B), etc.

With reference to the screen shots depicted in FIGS. 8D-8H, vaporizable material directed questions may, by way of example, include questions directed to: (1) identification of the vaporizable material as a whole; (2) the identification of the constituent elements or ingredients of the vaporizable material, such as an identifier or name (e.g., technical or common use names or identifiers) for flavors or strains, oils, type of cut, terpenes, solvents that comprise or constitute the vaporizable material or one or more of the constituent elements or ingredients thereof; (3) the amount and/or relative amounts of the constituent elements or ingredients of the vaporizable material, (4) identification of extraction method of the one or more of the constituent elements or ingredients of the vaporizable material; (5) identification of processing method (or aspects thereof such as maximum processing temperature, processing solvents, and processing ingredients) of the one or more of the constituent elements or ingredients of the vaporizable material.

Based on the individual and/or collective answers to these questions, the web-based programming system application generates a thermal profile that is defined to correspond to and effectuate the selected user experience taking into account: (1) the composition of the vaporizable material including, for example, the vaporization temperature and/or quantity of the constituent ingredients thereof and (2) the performance characteristics of the vaporizer device, such as the heater 320, which can effect such things as ramp-up and ramp down temperature gradients and heating capacity (see, e.g., FIG. 8J). A customers or users response relating to inhalation duration can be programmed to impacts/sets the length of the heating profile and thermal profile thereof. A customer's response to plume size/the degree of experience can be programmed to impact the temperature and duration of set points that correspond to vaporization of ingredients that impact the production of vapor. A customer's selection of intensity level may be programmed to impact the duration of the ramp-up and cool down times at the beginning and end of the inhalation such that the longer the ramp-up time the smoother the experience and the shorter the ramp-up time the more bold/harsh the user experience may be. The selection of oil strain can be programmed to correspond ingredients or components thereof that are understood to effectuate certain pharmacological effects or treatments.

Extraction method can impact the chemistry of the vaporization material and leave residual solvents that can become volatile at certain temperatures and may programmed to have an impact on the determination of a thermal ceiling or maximum temperature for the vaporizer. The customers selection of Terpene Partners can be corresponded to known strains from a reference table that identifies the terpene blend and their activation temperature for consideration in view of the user's experience preferences. Customer/user selection of dominant terpene allows the user to select/identify one or more terpenes (see FIGS. 8F-8G) that can be correlated in a reference table that identifies the terpene and its activation temperature and programmed into the generated thermal profile to effectuate the desired e user's experience preferences. The user's response to the identification and relative percentages of supplements or ingredients in the vaporizable material (see FIG. 8H) can be used to adjust set point temperatures and duration to vaporize to certain ingredients that based on the user experience responses the user wishes to be highlighted.

Further, it is herein contemplated that the initial generation of the a thermal profile by the web-based thermal profile programming software based on the user's responses to the foregoing queries may be subsequently adjusted, iteratively, via a user graphical user interface that allows the user to position and select click-able dots on the thermal profile chart (FIG. 8J) and move those dots in the x and y axis to adjust temperature and duration of set points and ramp-up and down times. Such an interactive interface is depicted in FIG. 8J1.

As noted above, the resulting generated thermal profile may in addition to including the set points and their duration and sequence, may also include a thermal ceiling or maximum temperature that is set below the vaporization temperature of a particular constituent ingredient, which to the extent contained within the vaporizable material, is not to be vaporized or vaporized in limited amounts. For example, it may be desirable to set a thermal ceiling to, at, or below the boiling point of Vitamin E acetate (e.g., 363 degrees Fahrenheit), the vaporization of which may negatively impact health. The thermal profile temperature ceiling could be implemented in the thermal profile to override and adjust a thermal profile that would otherwise be generated based on the responses to the questions that would result in a thermal profile that heats the vaporizable material above the thermal ceiling temperature. For example if the answer or combination of answers generates a desired temperature of 450 F with a thermal ceiling of 363 F, then any such set points above 363 F would be adjusted by the programming system software to a lower temperature, at or below the maximum thermal ceiling temperature of 363 F. The maximum thermal ceiling temperature can incorporate a fixed or variable safety margin to ensure that the thermal ceiling temperature is not reached or exceeded. The variable safety margin may be dependent on one or more of the following factors or conditions, including but not limited to altitude, external temperature, and regulatory differences based on geographic location or use environment.

Thermal profile recipes, such as those set forth in the thermal profile correlation tables depicted in FIG. 10, can be developed to correspond with a customer's responses to questions, such as those set forth above and illustrated in FIG. 8. As illustrated in the table set depicted in FIG. 10, each thermal profile table includes (1) a far right column that specifies a time duration segment, (2) a middle column that includes a corresponding temperature for each time end point specified in the far right column, and (3) a far left column that defines corresponding start and end points and ingredients and plume generation sequences that correspond to activation temperatures specified in the middle column. Each thermal profile correlation table set, such as the set illustrated FIG. 10, may be developed for (1) a particular vaporizer device to take into consideration the thermal properties and performance of the device, (2) a particular vaporizable material, (3) a user specified preferences (e.g., neutral intensity with a mild plume size), and (4) a maximum thermal ceiling temperature (e.g., 410 degrees Fahrenheit). Each table in the set of thermal profile correlation tables may, for example, be developed as illustrated in FIG.

Figure 11:
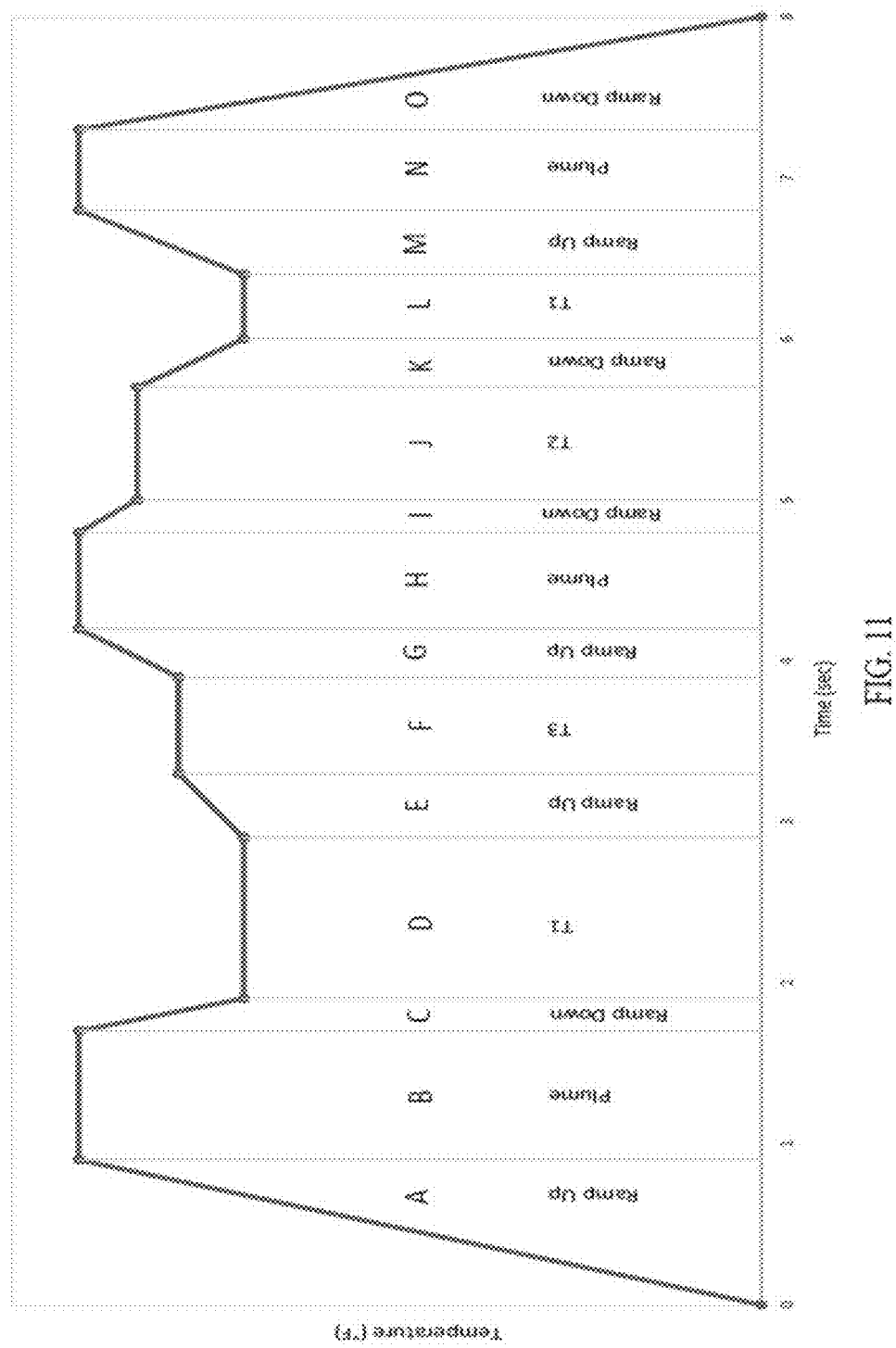
FIG. 11 is a depiction of a thermal profile that corresponds with one of the thermal profile recipes contained in the set of thermal profile correlation tables set forth in FIG. 10.

10, for a particular vaporizer device and vaporizable material so as to implement a specified user preference depending on inhalation duration. Thus, the table on the upper left of FIG. 10 corresponds to an inhalation duration of 2 seconds, with each successive table corresponding to an inhalation duration of one additional second, such that the last table in the set of tables depicted in FIG. 10, which is located on the bottom right corresponds to an inhalation duration of 10 seconds. Thus for example the 8.0 second inhalation duration table located at the bottom left of FIG. 10 corresponds to the heating and thermal profile depicted in FIG. 11. As illustrated in FIG. 11 each thermal profile may be broken up into block logic elements that correspond to a particular heating segment (e.g., A, B, C, . . . N, O) including their corresponding time segments and set points thereof in the thermal profile recipe. The block logic elements may be modified in temperature (or power) and/or time duration to effectuate the desired thermal profile or to adjust a selected thermal profile to fit within a specified inhalation duration or thermal ceiling temperature.

In the thermal profile correlation tables set forth in FIG. 10, each individual table corresponds to a thermal profile recipe for the same vaporizer device, vaporizable material, and the same user preferences, with the variable in the tables being inhalation duration. In implementation, a thermal profile generator application or logic may select or generate a thermal profile by correlating user inputs to a predetermined thermal profile recipe that corresponds with: (1) a particular vaporizer device to take into consideration the thermal properties and performance of the device, (2) a particular vaporizable material, (3) a user specified preferences (e.g., neutral intensity with a mild plume size), and/or (4) a maximum thermal ceiling temperature (e.g., 410 degrees Fahrenheit). Alternatively, a logic equation may be employed that correlates user inputs to heating segments of a thermal profile recipe taking into consideration: (1) the thermal properties and performance of a specific vaporizer device, (2) a specified vaporizable material, (3) user specified preferences (e.g., intensity, plume size, inhalation duration), and/or (4) a maximum thermal ceiling temperature (e.g., 410 degrees Fahrenheit). The logic equation may be developed from empirical analysis and/or from data or other specifications. For example, implementation or generation of the thermal profile in response to a customer's query responses may be premised on correlations between the particular ingredients of vaporizable materials and the particular use effects and vaporization or boiling point temperatures of that material. An example of such a correlations are set forth in the tables below.

TABLE 1

Terpene Flavors, Effects and Vaporization Temperatures

| Terpene | Flavor and Associated Effects | Boiling Point Temperature |
|---|---|---|
| Humulene | Flavor: Hops with a distinctive aroma. Effect: found in higher levels in sativa strains and is known for giving uplifting and energetic feelings. | 225 deg. F. |
| Pinene | Flavor: pine tree aroma. Effect: can provide body relaxation and sedative when combined with THC | 313 deg. F. |
| Myrcene | Flavor: Musky and earthy aroma. Effect: can tickle the nose | 334 deg. F. |
| Limonene | Flavor: Citrus lemon and orange aroma. Effect: Elevates mood and energy. Anti-fungal/anti-carcinogenic | 349 deg. F. |
| Eucalyptol | Flavor: Rosemary and *eucalyptus* smell. Effect: relaxation and centering effect | 351 deg. F. |

TABLE 2

Ingredient Activation Temperatures

| Ingredient Name | Activation Temp Fahrenheit | Activation Temp Celsius |
|---|---|---|
| Aldehyde | 383 | 195 |
| Alpha-Bisabolol | 311 | 155 |
| Alpha-Caryophyllene | 514 | 268 |
| Alpha-Phellandrene | 311 | 155 |
| Alpha-Pinene | 311 | 155 |
| Alpha-Terpinene | 311 | 155 |
| Alpha-Terponeol | 311 | 155 |
| Beta-Caryophyllene | 320 | 160 |
| Beta-Pinene | 331 | 166 |
| Big Plume | 415.5 | 213 |
| Bisabolol | 307 | 152 |
| Butyl Acetate | 259 | 126 |
| Camphene | 331 | 166 |
| Caryophyllene-Oxide | 311 | 155 |
| CBC (Activation) | 428 | 220 |
| CBD (Activation) | 356 | 180 |
| CBDa (Activation) | 284 | 140 |
| CBE (Activation) | 383 | 195 |
| CBN (Activation) | 356 | 185 |
| Cedrene | 311 | 155 |
| Cis-3-hexenol | 313 | 156 |
| Cis Beta-Ocimene | 388 | 198 |
| Citral | 311 | 155 |
| Citronellal | 311 | 155 |
| Citronellol | 388 | 198 |
| D-Camphor | 334 | 168 |
| Delta-3-Carene | 331 | 166 |
| Discreet | 365.5 | 185 |
| Ethyl Butyrate | 249 | 120 |
| Ethyl Methyl Phenyl Glycidate | 521 | 271 |
| End | 250 | 121 |
| Ethyl Isovalerate | 271 | 132 |
| Ethyl Maltol | 554 | 290 |
| Farnesene | 311 | 155 |
| Fenchyl | 334 | 168 |
| Geraniol | 388 | 198 |
| Geranyl Acetate | 473 | 245 |
| Humulene | 388 | 197 |
| Isoamyl Acetate | 285 | 140 |
| Isoborneol | 334 | 168 |
| Limonene | 349 | 176 |
| Linalool | 388 | 197 |
| L-Menthol | 334 | 168 |
| Mild Plume | 390.5 | 199 |
| Myrcene | 334 | 167 |
| Nerol | 396 | 202 |
| b-Ocimene | 150 | 65 |
| Pulegone | 435 | 223 |
| Sabinene | 514 | 268 |
| Sessionable | 365.5 | 185 |
| Styrallyl Acetate | 203 | 95 |
| Terpineol | 426 | 219 |
| Terpinolene | 361 | 183 |
| THC (Activation) | 428 | 220 |
| Trans Beta-Ocimene | 388 | 198 |
| Valencene | 349 | 176 |

| Ingredient Activation Temperatures and Treatment Uses | | | | | | |
|---|---|---|---|---|---|---|
| TEMPERATURES | TEMPERATURES | CANNABINOIDS | TREATMENTS | + | COMPOUNDS | TREATMENTS |
| Range 60°-125° c. 120° c. | Range 140°-275° f. 248° f. | Tetrahydrocannabinol THCA Acid Conversion | 1) Requires 30 mins. in the oven. 2) When eaten raw (Unheated): Anti-inflammatory. Anti-epileptic, and Anti-proliferic. | + | Cannabigerol CBG (Converted CBGA) | Conversion occurs while curing Anti-inflammatory Analgesic, Anti-bacterial Anti-fungal, Bone stimulant, and Anti-proliferic |
| Range 80°-135° c. 130° c. | Range 176°-275° f. 266° f. | Cannabidiol CBDA Acid Conversion | 1) Requires 60 mins. in the oven. 2) When eaten raw (Unheated): Anti-proliferic, and Anti-inflammatory. Not fully elucidated | + − | β-caryopyllene $1^{st}$ Med Vapor During CBD conversion | Anti-malarial Cytoprotective, and Anti-inflammatory Increases CBD, and CBE content. |
| Range 100°-145° c. 140° c. | Range 212°-293° f. 248° f. | Cannabichromene CBCA Acid Conversion | 1) Requires 60 mins. in the oven. 2) When eaten raw (Unheated): Anti-bacterial, and Anti-fungal. Not fully elucidated | + − | β-sitosterol $2^{nd}$ Med Vapor During CBD conversion | Anti-inflammatory, and 5-α-reductase inhibitor Increases CBD, and CBE content. |
| Boil Point 157° c. 155° c. | Boil Point 315° f. 311° f. | Tetrahydrocannabinol THC Delta 9 (Δ-9) | Anti-inflammatory, Appetite stimulant Anti-emetic, Anti-proliferic, and Anti-oxidant | + − | α-pinene Daytime Meds | With CBD, treats MRSA, Anti-inflammatory, Bone stimulant, Anti-biotic, Broncodilator, and Anti-neoplastic |
| Range 160°-180° c. 165 c. | Range 320°-356° f. 329° f. | Cannabidiol CBD Excludes Δ-8 | Most conditions listed, excluding the following: Anti-insomnia, Anti-fungal, and Appetite stimulant | + − + | β-myrcene Daytime Meds Δ-3-carene | Analgesic, Anti-bacterial Anti-mutagenic, and Anti-inflammatory Anti-inflammatory |
| Boil Point 177° c. 175° c. | Boil Point 351° f. 347° f. | Tetrahydrocannabinol THC Delta 8 (Δ-8) | The Δ-8 cannabinoid model lead to the HU-210 from Hebrew University. Non-psychoactive Neuroprotective, And, Anti-emetic | + + + + | eucalyptol limonene ρ-cymene apignenin | Blood flow stimulant. Anti-depressant, & Agonist. Anti-biotic, & Anti-candidal. Estrogenic, & Anxiolitic. |
| Boil Point 185° c. 185° c. | Boil Point 365° f. 365° f. | Cannabinol CBN THC degradation | CBN increases with the prolonged exposure to heat, oxygen, and time Anti-spasmodic Anti-inflammatory, and Analgesic. | + − | Cannaflavin A Nighttime Meds NORMI. Favorite | COX inhibitor, and LO inhibitor. Pending device temperature error. |
| Boil Point-Theory 195° c. | Boil Point-Theory 383° f. | Cannabielsoin CBE CBD degradation | CBE increases with the prolonged exposure to heat, oxygen, and time Likely to contain cannabinoids other than CBE. Intended to show the maximum medicinal temperature. | + − | llinalool Nighttime Meds Club Favorite | Sedative, Anti-depressant, Anxiolytic, and Immune potentiator (like limonene) |

-continued

Ingredient Activation Temperatures and Treatment Uses

| TEMPERATURES | TEMPERATURES | CANNABINOIDS | TREATMENTS | +/− | COMPOUNDS | TREATMENTS |
|---|---|---|---|---|---|---|
| High Benzene Level 205° c. | High Benzene Level 401° f. | * Hydro-carbons * Benzene * Avoid Vapors* | WARNING Toxic Vapors at 392° f. Harmful smoke toxins begin: https://www.canorml.org/vaporizors/ | + − − | terpinen-4-ol Smoke ≥ Vapor borneol | Anti-biotic, and AChE inhibitor Anti-biotic (Like ρ-cymene.) |
| Boil Point <220° c. 220° c. | Boil Point <428° f. 428° f. | Tetrahydro-cannabivarin THCV Blocks THC | Euphoriant, Anti-THC. Analgesic Anti-diabetic Anorectic, and Bone-stimulant | + − − | α-terpineol Smoke ≥ Vapor Ready to consume | Sedative, Anti-biotic Anti-oxidant, and Anti-malarial Reduce toxins by consuming. |
| Boil Point <220° c. 220° c. | Boil Point <428° f. 428° f. | Cannabi-chromene CBC Blocks THC | Anti-proliferative Anti-bacterial, Bone stimulant, Anti-inflammatory, and Analgesic | + + − | pulegone quercetin Smoke ≥ Vapor | Sedative, Anti-pyretic, Anti-multigenic, Anti-viral, Anti-oxidant, and Anti-neoplastic |

It should be understood that while a designated programing device 601 is described above to program the vaporizable material cartridges 300 with a recipe code 350, the process embodied in FIGS. 5-11, may be performed using a vaporizer body 200 to program the thermal profile recipe code 350 of the cartridge 300, such as previously described. In which case the programing device 601 of the thermal profile programing system depicted in FIG. 6 may be comprised of the vaporizer body 200 that is configured to program the vaporization cartridge 300 with a desired thermal and overall heating profile. The thermal and overall heating profile may reside on the vaporizer body 200 and/or be communicated thereto by an electronic device 700 and/or remote server 800 via a wired or wireless connection, as illustrated in FIGS. 2A-2B. Once communicated to the vaporizer body 200, the thermal profile may be stored in memory 290 and used to control the heating of the cartridge 300 and/or communicated and encoded into the recipe code 350 for that cartridge 300. The programmed vaporizer cartridge 300 could then be detached from the vaporizer body 200 that programmed it and be used with a different a vaporizer body 200 (than the vaporizer that encoded the cartridge 300) while retaining and using the newly encoded thermal profile recipe code 350 to control the heating and thermal profile. The process may be repeated for different vaporizer cartridges 300 that contain different vaporizable material and ingredients. Each vaporizer cartridge 300 would therefore retain a custom programmed thermal profile recipe code 350 that dictates the heating and thermal profile for that particular cartridge 300. The user could swap out one cartridge 300 for another differently programmed cartridge 300 while retaining the desired thermal profile for consumption of the vaporizable material in each cartridge 300. A supplier could use the programming system to select/define a particular thermal profile for a supplier's particular vaporizable material and cartridge and order from the cartridge manufacture mass volumes of cartridges 300 pre-programmed/encoded with the supplier's selected/defined thermal profile recipe code 350 to pack with the supplier's vaporizable material.

With reference to the screen shot depicted in FIG. 8L, the resulting thermal profile generated by the programming system may be programed to be dynamic or adaptive based on use data. For example, ingredients of a vaporizable material that have lower vaporization temperatures will deplete at a higher rate than ingredients with higher vaporization temperatures because lower vaporization temperature ingredients are vaporized, and hence depleted, at any temperature at or above their vaporization temperature while higher vaporization temperature ingredients are only vaporized or depleted at temperatures that also deplete lower vaporization temperature ingredients. When the relative amount of an ingredient is sufficiently depleted, the user may experience a change in the flavor or user experience. The degree of depletion of a given ingredient can be calculated based on inhalation count and/or cumulative inhalation duration, which inputs can be used to effectuate dynamic adjustments of the thermal profile, to add additional set points, increase or decrease the set point temperatures and/or durations, and/or re-sequence set points that define the thermal profile.

Use data, such as inhalation count and/or cumulative inhalation duration, may be counted and/or tracked by the vaporizer body 200 using sensors 260, such as flow sensors, and/or calculated using the thermal profile for each inhalation and used to control the heating profile for subsequent inhalations including whether to send any power to the pod/cartridge 300. Such use data may be (1) retained in memory 290 of the vaporizer body 200, (2) communicated and written/encoded to memory contained on the vaporizer cartridge 300, and/or (3) communicated to a an external device such as the electronic device 700 and/or the remote server 80. Use and depletion tracking of a pod/cartridge 300 can be used to preclude unauthorized refilling or reuse of the pod/cartridge 300. For example, by tracking use data and encoding such use data on the pod/cartridge 300 being used, such information may be communicated to the vaporizer body 200 from the pod/cartridge 300 to impact control of the power delivered to the pod/cartridge 300.

Thus for example, if the use data encoded on the pod/cartridge 300 indicates that the pod/cartridge 300 was previously depleted (e.g., for example by counting aggregate inhalations or inhalation duration), the pod/cartridge 300 would be identified or encoded as inactive and the vaporizer base 200 would recognize that the pod/cartridge 300 was so designated and the controller 220 therein would not allow power to the pod/cartridge 300, thereby rendering the pod/cartridge unusable. Because the use data corresponding to the level of depletion of the pod/cartridge 300 is encoded onto the pod/cartridge 300, the user cannot impermissibly extend the use or bypass unauthorized reuse of a pod/cartridge 300 by removing and attaching the pod/cartridge 300 to another vaporizer base or body 200 because the new vaporizer base 200 would continue to write/encode use data to the pod/cartridge and communicate with the pod/cartridge 300 to determine whether it is designated as inactive or depleted. Upon the vaporizer base's receipt of a communication indicative that the pod/cartridge 300 is inactive or depleted, the controller 220 will not allow power to the pod/cartridge 300 and as such it will be unusable with any compatible vaporizer 100. Hence, by documenting a cartridge's cumulative inhalation count, cumulative inhalation duration and received cumulative power, and encoding that documentation onto the cartridge 300, manufacturer control over impermissible use of the cartridge 300 can be exercised so that cartridges 300 are not overused, reused by filling them with uncontrolled or impermissible materials.

Additionally, a calculation may be used to further refine the accuracy of cumulative hit count or cumulative hit duration by tracking the power delivery for each inhalation. For example, if a six (6) second inhalation duration employs a relative low power/temperature thermal profile for the first 3 seconds and a relative high thermal profile for the second 3 seconds, the depletion rate of the cartridge 300 will be effected. By calculating the area under the thermal profile (e.g., the area under FIGS. 3A, 3B, 8J, 8J1, 11) for each inhalation and correlating that to a depletion rate, the depletion rate of the cartridge 300 can be calculated and the state of depletion of the cartridge 300 can be specified and recorded on the cartridge 300.

Similarly, use data may be employed to effectuate an adaptive or dynamic thermal profile that changes with use over time. For example, a thermal profile initially may include a set point that activates ingredient XYZ at a temperature of 250° F., while all other set point segments of the thermal profile are between temperatures of 300° F.-350° F. After 300 seconds of cumulative vaporization, it is calculated or otherwise determined that ingredient XYZ is sufficiently depleted. The thermal profile going forward for that pod/cartridge may be programmed to automatically change the set point temperature and or segment duration, either gradually over a number of vaporization cycles or abruptly, to 300° F. in order to activate the next lowest temperature ingredient in the vaporizable material. Programming the thermal profile in a dynamic manner to take into account use data and/or other inputs or data may be implemented in many different ways and may result in adjustments in the number of set points, set point temperatures, set point durations, set point sequence, ramp up and ramp down times and set point transition profiles and may also impact the overall thermal profile or heating profile duration and may do so independently or in combination of one or more of the foregoing. The manner by which a given thermal profile is adjusted with use may take into consideration the user preferences and/or the composition of the vaporizable material so that the user experience is maximized even as the pod/cartridge is being depleted or used.

The sensors 260 may be employed to recognize the changing status or performance of the vaporizer and/or pod/cartridge 300 and adjust and/or deactivate a malfunctioning vaporizer body 200 and/or pod/cartridge 300. For example a short circuit, broken heating element in the pod/cartridge 300, an out of range heater resistance can be sensed by a corresponding sensor 260, written to memory of the pod/cartridge and/or vaporizer body, and used to deactivate one or both components from further use. Alternatively, as the battery power is depleted, the performance of the vaporizer 100 may change, the changes in performance due to battery depletion may be characterized and programmed into the thermal profile recipe code 350 or vaporizer body 200 to adaptively change the thermal profile to take into account the changes in performance of the vaporizer 100.

Further, while the web-based thermal profile programming system software described above contemplates that in one embodiment the resulting thermal profile is generated to work on a vaporizer device with pre-selected performance characteristics, it is contemplated that the responses to the individual and/or collective answers to the user experience and/or vaporizable material queries may be incompatible with the pre-selected performance characteristics of the vaporizer 100. To account for such issues, the thermal profiling programming system software may be programmed to advise the customer, in response to a customer's response to the queries, that a vaporizer device 100 with greater heating capacity and/or the ability to effectuate steeper heating and/or cooling gradients would be required and recommend one or more alternative vaporizer device 100 systems. In this regard, the web-based thermal profiling programming system software described above (e.g., in connection with FIGS. 5-11), may include a screen that provides the customer the option to select or identify a vaporizer device 100 system for use with the customer's vaporizable material. Once selected, the thermal profile generated by thermal profile programming system would be specific to the vaporizer device selected by the customer.

In order to determine the validity of the pod cartridge 300 for development applications as well as use in production, the cartridge may contain encrypted and/or unencrypted information that is validated and authenticated by the vaporizer body 200 to allow vaporizer use with the cartridge. Upon approval of cartridge 300 validity, the vaporizer body 200 will become responsive or operable such that to actions, including but not limited to providing power to the cartridge 300 to commence vaporization of the vaporizable material contained therein. If approval is not achieved, the vaporizer body may provide feedback to the user indicated that the inserted cartridge 300 into the vaporizer body 200 is not valid for use and the vaporizer body will not provide power to the cartridge 300, preventing vaporization to occur. The cartridge validation process may be implemented using an encryption key (comprised of random numbers) that is contained in the vaporizer cartridge 300 (e.g., in the recipe code 350) that is validated and authenticated every time the cartridge is inserted into a vaporizer body 200. By incorporating an encryption key into the cartridge that is required to be validated prior to use provides a protective element at the point of production or manufacture that is capable of mitigating against use of counterfeit cartridges.

While representative, the foregoing cartridge programming process and vaporizers 100, as noted above, are capable of providing many advantages to the end user and suppliers, including, but not limited to, facilitating testing of customized thermal profile settings in real-time and doing so without the presence of a sales representative for the vaporizer/pod manufacturer or supplier.

The foregoing disclosure describes by way of illustration and examples specific embodiments in which the subject matter may be implemented or practiced. It should be understood that other embodiments may be utilized and that structural and logical substitutions and changes may be made that fall within the scope of this disclosure, which is intended to cover any adaptations and variations of the various embodiments disclosed herein and combination of the various features and component elements thereof.

What is claimed is:

1. A thermal profile vaporizer programming system, comprising:
   a user fillable vaporizer cartridge that includes a reservoir containing vaporizable material, a heating component adapted for vaporizing the vaporizable material;
   a thermal profile programming device configured to program the cartridge; and
   a computing system configured to query vaporizer use preferences from a customer and in response to the use preferences selects a thermal profile corresponding to the use preferences from a set of thermal profiles and communicates the thermal profile to the thermal profile programming device.

2. The thermal profile vaporizer programming system of claim 1, wherein the thermal profile programming device has a receptacle for receiving the vaporizer cartridge.

3. The thermal profile vaporizer programming system of claim 2, wherein the cartridge receptacle has one or more electrical contacts configured to engage with the vaporizer cartridge when the vaporizer cartridge is inserted into the receptacle of the thermal profile programming device.

4. The thermal profile vaporizer programming system of claim 1, wherein the thermal profile programming device encodes the thermal profile from the computing system onto a recipe code of the vaporizer cartridge.

5. The thermal profile vaporizer programming system of claim 4, wherein the thermal profile communicated by the computing system to the thermal profile programming device is encrypted.

6. The thermal profile vaporizer programming system of claim 5, wherein the thermal profile is decoded by the thermal profile programming device prior to being encoded onto the recipe code.

7. The thermal profile vaporizer programming system of claim 1, wherein the thermal profile programming device further includes a thermal profile generator application.

8. The thermal profile vaporizer programming system of claim 1 further comprising a local computer configured to interact with the thermal profile programming device by the customer.

9. The thermal profile vaporizer programming system of claim 1, wherein the customer interacts with the thermal profile programming device through the computing system.

10. The thermal profile vaporizer programming system of claim 9, wherein the computing system has a thermal profile generator application, a user database and a thermal profile database.

11. The thermal profile vaporizer programming system of claim 1, wherein the thermal profile is configured to extend across a series of multiple user inhalations.

12. The thermal profile vaporizer programming system of claim 1, wherein the thermal profile is configured to extend across only a single inhalation.

13. A computerized method of using a thermal profile vaporizer programming system, the method comprising:
   requesting, by a customer, a use of the thermal profile vaporizer programming system;
   sending the customer a thermal profile programming device and a development vaporizer comprising a vaporizer body and fillable development vaporizer cartridges;
   filling, by the customer, one of the development vaporizer cartridges with a customer selected vaporizable material;
   interfacing, by the customer, with a thermal profile programming system application residing on a remote computing system;
   validating, by the remote computing system, authenticity of the thermal profile programming device, the development vaporizer and the fillable development vaporizer cartridges;
   providing, by the customer, information regarding the vaporizable material and vaporizer use preferences;
   generating, by the thermal profile programming system application, a thermal profile to correspond with the information provided by the customer regarding the vaporizable material and vaporizer use preferences;
   communicating, by the remote computing system, the thermal profile to the thermal profile programming device;
   encoding, by the thermal profile programming device, the thermal profile onto the development vaporizer cartridge;
   testing, by the customer, the development vaporizer cartridge encoded with the thermal profile; and
   ordering, by the customer, the development vaporizer cartridge encoded with the thermal profile.

14. The method of claim 13, wherein the customer requests the use of the thermal profile vaporizer programming system by opening a customer account.

15. The method of claim 13, wherein the vaporizable material is an oil.

16. The method of claim 13, wherein the validating process is accomplished by reading and validating an unique identification pre-loaded onto a memory of the programming device.

17. The method of claim 16, further comprising:
   unlocking the programming device by a code sent by the programming system application upon validation.

18. The method of claim 13, further comprising:
   removing the programmed/encoded cartridge from the programming device.

19. The method of claim 18, wherein the testing process is accomplished by inserting the programmed/encoded cartridge into the vaporizer body.

20. A computerized method of using a thermal profile vaporizer programming system, the method comprising:
   receiving, from a client device, a customer request to use a thermal profile vaporizer programming system;
   validating authenticity of a thermal profile programming device and a development vaporizer that are in the customer's possession, the development vaporizer comprising a vaporizer body and a fillable development vaporizer cartridge;
   receiving, from the client device, information regarding a vaporizable material included in the development vaporizer cartridge and vaporizer use preferences;
   generating, by a thermal profile programming system application, a thermal profile to correspond with the information received from the customer regarding the vaporizable material and vaporizer use preferences;
   communicating the thermal profile to the thermal profile programming device; and
   encoding, by the thermal profile programming device, the thermal profile onto the development vaporizer cartridge.

* * * * *